(12) United States Patent
Kim et al.

(10) Patent No.: US 9,538,099 B2
(45) Date of Patent: Jan. 3, 2017

(54) X-RAY IMAGING APPARATUS AND CONTROL METHOD THEREOF

(71) Applicant: SAMSUNG ELECTRONICS CO., LTD., Suwon-si, Gyeonggi-do (KR)

(72) Inventors: Dong-Hyuk Kim, Hwaseong-si (KR); Dong Hun Lee, Hwaseong-si (KR); Tae Ho Lee, Hwaseong-si (KR); Man Seung Cho, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/608,696

(22) Filed: Jan. 29, 2015

(65) Prior Publication Data

US 2016/0061966 A1 Mar. 3, 2016

(30) Foreign Application Priority Data

Aug. 27, 2014 (KR) ........................ 10-2014-0112621

(51) Int. Cl.
*H04N 5/32* (2006.01)
*A61B 6/00* (2006.01)

(52) U.S. Cl.
CPC ............... *H04N 5/32* (2013.01); *A61B 6/4233* (2013.01); *A61B 6/5205* (2013.01); *A61B 6/542* (2013.01)

(58) Field of Classification Search
CPC ............. G01T 1/24; G01T 1/247; H04N 5/32; A61B 6/4233
See application file for complete search history.

(56) References Cited

U.S. PATENT DOCUMENTS

| 8,983,035 | B2* | 3/2015 | Noma ...................... H05G 1/64 250/214 DC |
| 2011/0199523 | A1* | 8/2011 | Tanabe .................... G01T 1/244 348/300 |
| 2013/0140467 | A1* | 6/2013 | Kitano ............. H01L 27/14663 250/393 |

\* cited by examiner

*Primary Examiner* — David Porta
*Assistant Examiner* — Faye Boosalis
(74) *Attorney, Agent, or Firm* — Staas & Halsey LLP

(57) ABSTRACT

Disclosed herein is an X-ray imaging apparatus including: a gate driver configured to apply a turn-on signal to a plurality of gate lines; and a readout circuit configured to read out a signal from the plurality of gate lines, wherein if an X-ray signal is detected from a gate line of the plurality of gate lines, the gate driver changes a turn-on time period of the turn-on signal.

19 Claims, 27 Drawing Sheets

(a)

(b)

(a)

(b)

(a)

(b)

X-RAY IMAGING APPARATUS AND CONTROL METHOD THEREOF

CROSS-REFERENCE TO RELATED APPLICATIONS

This application claims the benefit of Korean Patent Application No. 10-2014-0112621, filed on Aug. 27, 2014, in the Korean Intellectual Property Office, the disclosure of which is incorporated herein by reference.

BACKGROUND

1. Field

Embodiments of the present disclosure relate to an X-ray imaging apparatus of producing images about the inside of an object by irradiating X-rays onto the object, and a control method of the X-ray imaging apparatus.

2. Description of the Related Art

An X-ray imaging apparatus is equipment for acquiring images about the inside of an object by irradiating X-rays onto the object and receiving the X-rays transmitted through the object. Since various materials of or configuring an object have different degrees of X-ray radiolucency according to their properties, the inside structure of the object can be imaged by detecting the strengths or intensities of X-rays transmitted through the object.

If a generator part is not electrically connected to a detector part in an X-ray imaging apparatus, a process of detecting X-rays to determine existence of X-rays before extracting X-rays is needed. The process is called Auto Exposure Detection (AED). X-rays are detected by using an X-ray detection sensor, or by a method of determining existence of X-ray successively for individual rows in an X-ray detection region formed in an array of rows and columns. After detecting X-rays, the X-ray imaging apparatus extracts signals of an actual X-ray image. A process of detecting existence of X-rays and detecting X-rays in an X-ray detection region in order to acquire actual X-ray image signals is called readout. However, during the readout to detect X-rays, leakage or current trap may occur in which current or signals leak out due to the physical or chemical properties of devices. In this case, during the readout to acquire actual X-ray image signals, signal loss and a level difference of an X-ray image may occur.

SUMMARY

Therefore, it is an aspect of the present disclosure to provide an X-ray imaging apparatus of performing slow scanning for detecting X-rays on a predetermined region and fast scanning on the remaining region in a process of detecting X-rays in order to reduce a level difference of an X-ray image, and a control method of the X-ray imaging apparatus.

It is another aspect of the present disclosure to provide an X-ray imaging apparatus of performing general scanning for detecting X-rays on a predetermined region and binning scanning on the remaining region in a process of detecting X-rays in order to reduce a level difference of an X-ray image, and a control method of the X-ray imaging apparatus.

Additional aspects of the disclosure will be set forth in part in the description which follows and, in part, will be obvious from the description, or may be learned by practice of the disclosure.

In accordance with one aspect of the present disclosure, an X-ray imaging apparatus includes: a gate driver configured to apply a turn-on signal to a plurality of gate lines; and a readout circuit configured to read out a signal from the plurality of gate lines, wherein if an X-ray signal is detected from a gate line of the plurality of gate lines, the gate driver changes a turn-on time period of the turn-on signal.

If the X-ray signal is detected from the gate line of the plurality of gate lines, the gate driver may reduce the turn-on time period of the turn-on signal.

The X-ray imaging apparatus may further include an X-ray detection region including a first region and a second region, wherein each of the first region and the second region includes a plurality of gate lines, and the gate driver applies a turn-on signal having a turn-on time period that is longer than or equal to a threshold time period, to the gate lines of the first region, and applies a turn-on signal having a turn-on time period that is shorter than the threshold time period to the gate lines of the second region.

The readout circuit may detect X-rays from the gate lines of the first region.

The first region may be located above or below the second region.

Each of the plurality of gate lines may be connected to a plurality of pixels arranged in a row direction.

The readout circuit may detect X-rays from the plurality of pixels, and the gate driver divides regions based on a gate line of a pixel from which X-rays are detected, and applies turn-on signals having different turn-on time periods to the respective regions.

If an X-ray signal is detected from a first gate line, the gate driver may change a turn-on time period of a turn-on signal that is applied to a second gate line adjacent to the first gate line.

If a predetermined time period elapses, the gate driver may again apply the turn-on signal to the plurality of gate lines.

A turn-on time period of the turn-on signal that is again applied may be longer than the turn-on time period of the turn-on signal changed by the gate driver.

In accordance with another aspect of the present disclosure, an X-ray imaging apparatus includes: a gate driver configured to apply a turn-on signal to a plurality of gate lines; and a readout circuit configured to read out a signal from the plurality of gate lines, wherein if an X-ray signal is detected from a gate line of the plurality of gate lines, the gate driver synchronizes a turn-on time of the turn-on signal to a predetermined time.

The X-ray imaging apparatus may further include an X-ray detection region including a first region and a second region, wherein each of the first region and the second region includes a plurality of gate lines, and the gate driver applies the turn-on signal to the gate lines of the first region, sequentially, and applies a turn-on signal having a turn-on time synchronized to the predetermined time to the gate lines of the second region.

The first region may be located above or below the second region.

Each of the plurality of gate lines may be connected to a plurality of pixels arranged in a row direction.

If an X-ray signal is detected from a gate line of the plurality of gate lines, the gate driver may synchronize the turn-on time of the turn-on signal according to a predetermined binning pattern.

The readout circuit may detect X-rays from the plurality of pixels, and the gate driver may divide regions based on a gate line of a pixel from which X-rays are detected, and applies turn-on signals having different turn-on times to the respective regions.

If a predetermined time period elapses, the gate driver may again apply the turn-on signal to the plurality of gate lines.

In accordance with another aspect of the present disclosure, a control method of an X-ray imaging apparatus includes: applying a turn-on signal to a plurality of gate lines; and changing a turn-on time period of the turn-on signal if an X-ray signal is detected from a gate line of the plurality of gate lines.

The changing of the turn-on time period of the turn-on signal may include reducing the turn-on time period of the turn-on signal if the X-ray signal is detected from the gate line of the plurality of gate lines.

The X-ray imaging apparatus may include an X-ray detection region including a first region and a second region, each of the first region and the second region includes a plurality of gate lines, the applying of the turn-on signal to the plurality of gate lines may include applying a turn-on signal having a turn-on time period that is longer than or equal to a threshold time period, to the first region, and the changing of the turn-on time period of the turn-on signal may include applying a turn-on signal having a turn-on time period that is shorter than the threshold time period, to the second region.

The first region may be located above or below the second region.

In accordance with another aspect of the present disclosure, a control method of an X-ray imaging apparatus includes: applying a turn-on signal to a plurality of gate lines; and synchronizing a turn-on time of the turn-on signal to a predetermined time if an X-ray signal is detected from a gate line of the plurality of gate lines.

The synchronizing of the turn-on time of the turn-on signal to the predetermined time may include applying a plurality of turn-on signals having turn-on times synchronized to the predetermined time.

The X-ray imaging apparatus may include an X-ray detection region including a first region and a second region, each of the first region and the second region may include a plurality of gate lines, the applying of the turn-on signal to the plurality of gate lines may include applying the turn-on signal to the gate lines of the first region, sequentially, and the synchronizing of the turn-on time of the turn-on signal to the predetermined time may include applying a turn-on signal having a turn-on time synchronized to the predetermined time to the gate lines of the second region.

The first region may be located above or below the second region.

The synchronizing of the turn-on time of the turn-on signal to the predetermined time may include applying a plurality of turn-on signals having different turn-on times synchronized to different times according to a predetermined binning pattern.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
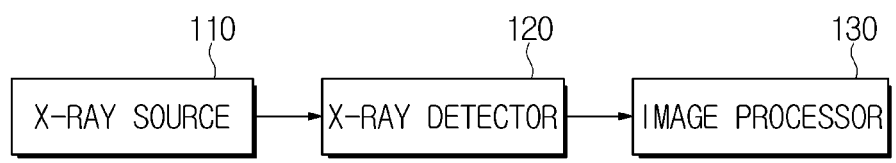
FIG. 1 is a control block diagram of an X-ray imaging apparatus according to an embodiment of the present disclosure.

Reference will now be made in detail to the embodiments of the present disclosure, examples of which are illustrated in the accompanying drawings, wherein like reference numerals refer to like elements throughout.

Hereinafter, an X-ray imaging apparatus and a control method thereof according to embodiments of the present disclosure will be described in detail with reference to the accompanying drawings.

Figure 2:
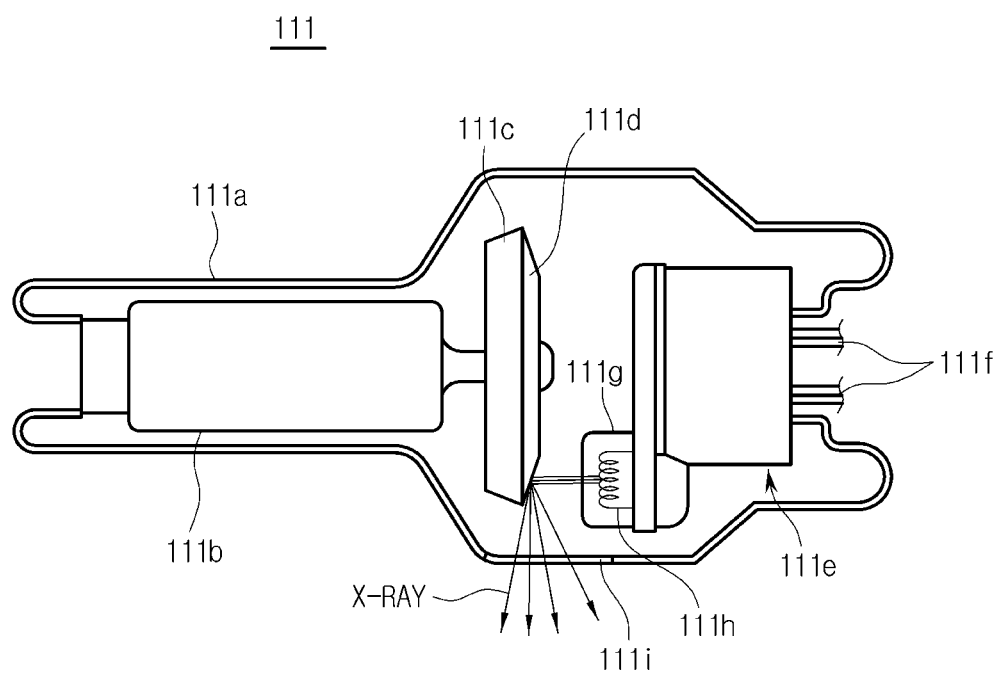
FIG. 2 illustrates an internal structure of an X-ray source.
Figure 3:
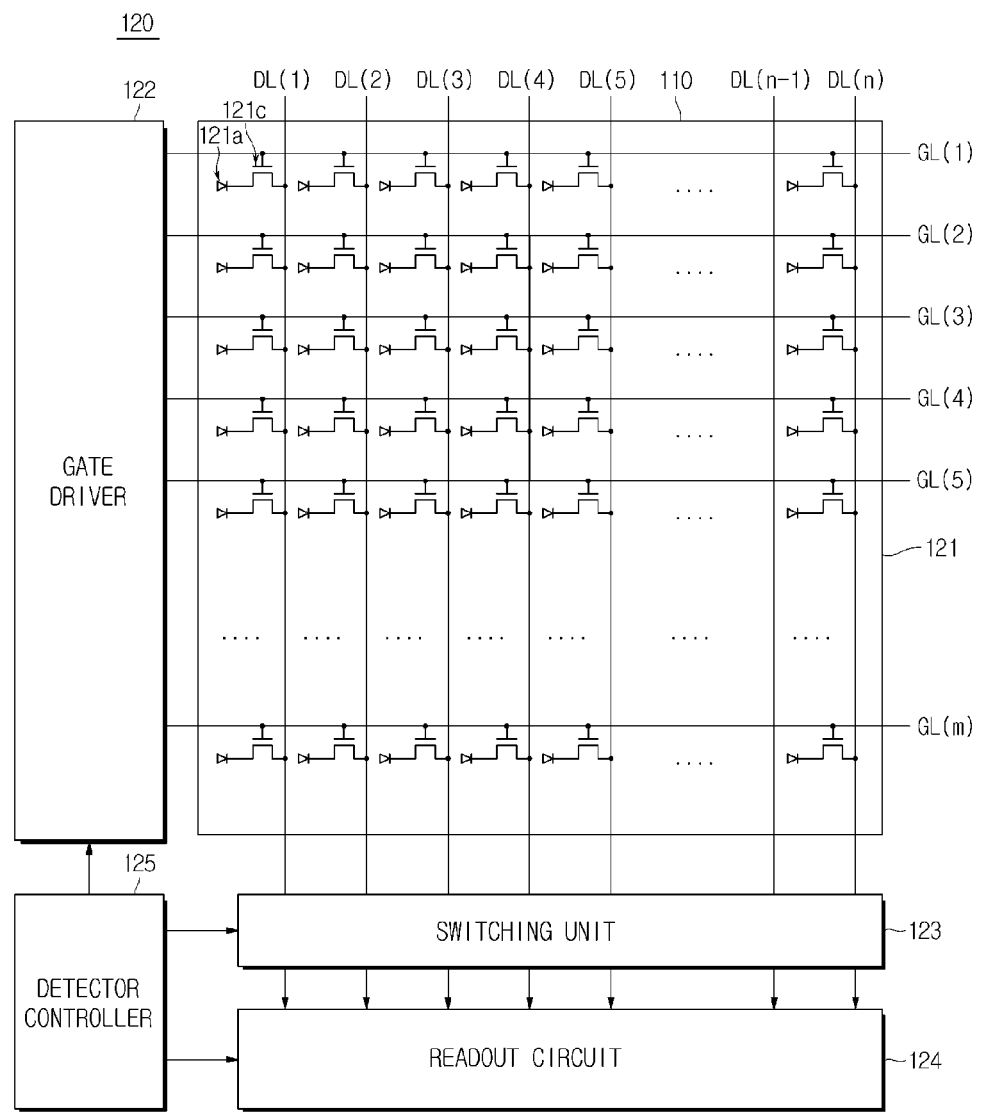
FIG. 3 is a circuit diagram briefly showing a circuit structure of an X-ray detector.

FIG. 1 is a control block diagram of an X-ray imaging apparatus according to an embodiment of the present disclosure, FIG. 2 illustrates an internal structure of an X-ray source, and FIG. 3 is a circuit diagram briefly showing a circuit structure of an X-ray detector.

Referring to FIG. 1, an X-ray imaging apparatus 100 according to an embodiment of the present disclosure may include an X-ray source 110 to generate and irradiate X-rays, an X-ray detector 120 to detect X-rays transmitted through an object, and an image processor 130 to produce an X-ray image about the inside of the object using the detected X-rays.

The X-ray source 110 may include an X-ray tube 111 to generate X-rays. Referring to FIG. 2, an anode 111b and a cathode 111e are provided in a glass tube 111a of the X-ray tube 111. The inside of the glass tube 111a is evacuated to a high vacuum state, and the filament 111h of the cathode 111e is heated to generate thermoelectrons. The filament 111h may be heated by applying current to electrical leads 111f connected to the filament 111h. The cathode 111e may include the filament 111h, and a focusing electrode 111g for focusing electrons. The focusing electrode 111g is also called a focusing cup.

When a high voltage is applied between the anode 111b and the cathode 111e, thermoelectrons are accelerated and collide with a target material 111d of the anode 111b, thereby generating X-rays. The target material 111d may be a high-resistance material, e.g., Cr, Fe, Co, Ni, W, or Mo. The generated X-rays are irradiated to the outside through a window 111i. The window 111i may be a Beryllium (Be) thin film.

The voltage that is applied between the anode 111b and the cathode 111e is called a tube voltage. The magnitude of a tube voltage may be expressed as a crest value (kVp). When the tube voltage increases, velocity of thermoelectrons increases accordingly. Then, energy (energy of photons) of X-rays that are generated when the thermoelectrons collide with the target material 111d also increases. A filter may be placed in an X-ray irradiation direction to adjust energy of X-rays. More specifically, a filter (not shown) for filtering a specific wavelength band of X-rays may be provided on the front or rear side of the window 111i to filter a specific energy band of X-rays. For example, by providing a filter made of aluminum or copper to filter out a low energy band of X-rays, it is possible to increase energy of X-rays that are irradiated.

Current flowing through the X-ray tube 111 is called tube current, and can be expressed as an average value (mA). When tube current increases, a dose of X-rays (that is, the number of X-ray photons) increases. In summary, energy of X-rays can be controlled by adjusting a tube voltage, and a dose of X-rays can be controlled by adjusting tube current and an X-ray exposure time.

Referring to FIG. 3, the X-ray detector 120 may include a detection region 121 to detect X-rays and to convert the detected X-rays into electrical signals, a gate driver 122 to apply driving signals to the detection region 121, a readout circuit 124 to read out electrical signals corresponding to intensities of X-rays from the detection region 121, a switching unit 123 to connect the detection region 121 to the readout circuit 124, and a detector controller 125 to control the gate driver 122, the switching unit 123, and the readout circuit 124.

Although not shown in FIG. 3, an Analog-to-Digital Converter (ADC) may be provided at an output terminal of the X-ray detector 120 to convert analog signals output from the readout circuit 124 into digital signals and transfer the digital signals to the image processor 130.

As methods for converting X-rays detected by the detection region 121 into electrical signals, there are a direct conversion method and an indirect conversion method.

In the direct conversion method, if X-rays are incident to the detection region 121, electron-hole pairs are temporarily generated in a light receiving device included in the detection region 121, electrons move to the anode 111b (see FIG. 2) and holes move to the cathode 111e (see FIG. 2) by an electric field applied to both terminals of the light receiving device, and the readout circuit 124 reads out the movements of the electrons or holes as electrical signals. In the direct conversion method, the light receiving device may be a photoconductor made of amorphous selenium (a-Se), CdZnTe, $HgI_2$, or $PbI_2$.

In the indirect conversion method, the detection region 121 further includes a scintillator. If irradiated X-rays react with the scintillator to be converted into visible rays, the light receiving device detects the visible rays, and converts the visible rays into an electrical signal. In the indirect conversion method, the light receiving device may be a photodiode made of a-Si, and the scintillator may be a GADOX scintillator of a thin film type, or a CSI (TI) of a micro pillar type or a needle type.

The X-ray imaging apparatus 100 can use any one of the direct conversion method and the indirect conversion method, and in the following embodiment, it is assumed that the X-ray imaging apparatus 100 uses the indirect conversion method.

The detection region 121 may include m×n (row×column) pixels arranged two-dimensionally. Each pixel may include a photodiode 121a to generate charges corresponding to an intensity of incident X-rays, and a transistor 121c that is turned on to make charges stored in the photodiode 121a flow to a data line DL or turned off to prevent the stored charges from flowing to the data line DL.

The transistor 121c may be a Thin Film Transistor (TFT). However, the transistor 121c is an example of a switching device, and another switching device may be used.

If X-rays incident to the X-ray detector 120 are converted into visible rays by the scintillator (not shown) and the visible rays arrive at the photodiode 121a, the photodiode 121a may generate an amount of charges corresponding to an intensity of the visible rays. The generated charges may be stored in the photodiode 121a. At this time, current or signals may leak out due to the physical properties of the photodiode 121.

If a turn-on signal is input to the transistor 121c, charges stored in the photodiode 121a flow to a data line DL, and if no turn-on signal is input to the transistor 121c, the transistor 121c may be maintained in a turned-off state so that charges are accumulated in the photodiode 121a.

If a voltage signal of a predetermined magnitude or more is applied to the gate of the transistor 121c, charges stored in the photodiode 121a may flow from the source of the transistor 121c to the drain of the transistor 121c. A voltage signal that is applied to the gate of the transistor 121c in order to turn on the transistor 121c is referred to as a turn-on signal or a gate signal.

The transistors 121c may be connected to each other by gate lines GL for each row, and by data lines DL for each column. In the example of FIG. 3, n transistors 121c arranged in a row may be connected to each other by a gate line GL, and m transistors 121c arranged in a column may be connected to each other by a data line DL. In this case, leakage and current trap may occur in the transistors 121c, as in the photodiodes 121a.

The gate driver 122 may apply a gate signal to m gate lines GL1, GL2, . . . , GLm, sequentially. If the gate driver 122 applies a gate signal, that is, a turn-on signal to a gate line GL, n transistors 121c connected to the corresponding gate line GL may be turned on so that charges stored in photodiodes 121a of the corresponding pixels flow to the data lines DL through the transistors 121c. The charges of the data lines DL may be read out by the readout circuit 124, and the ADC circuit may convert the read-out signal, that is, an analog signal into a digital signal.

That is, the X-ray detector 120 detects X-rays and acquires actual X-ray image signals by scanning the m gate lines GL.

Figure 4:
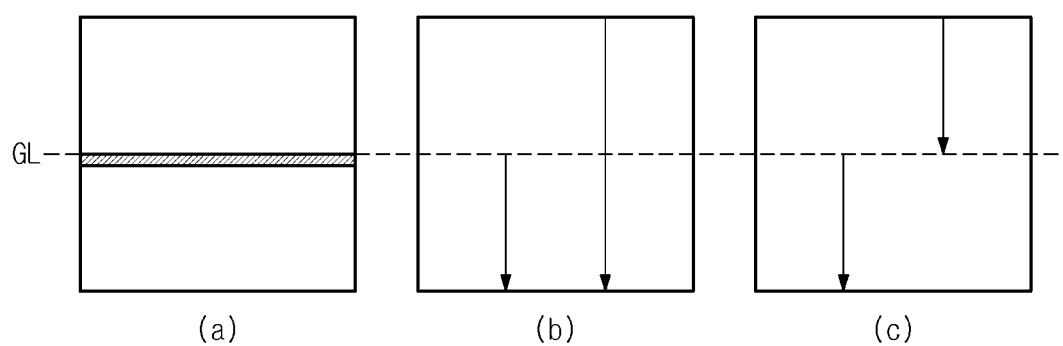
FIG. 4 is a view for describing a general gate scan method of an X-ray detector.
Figure 5:
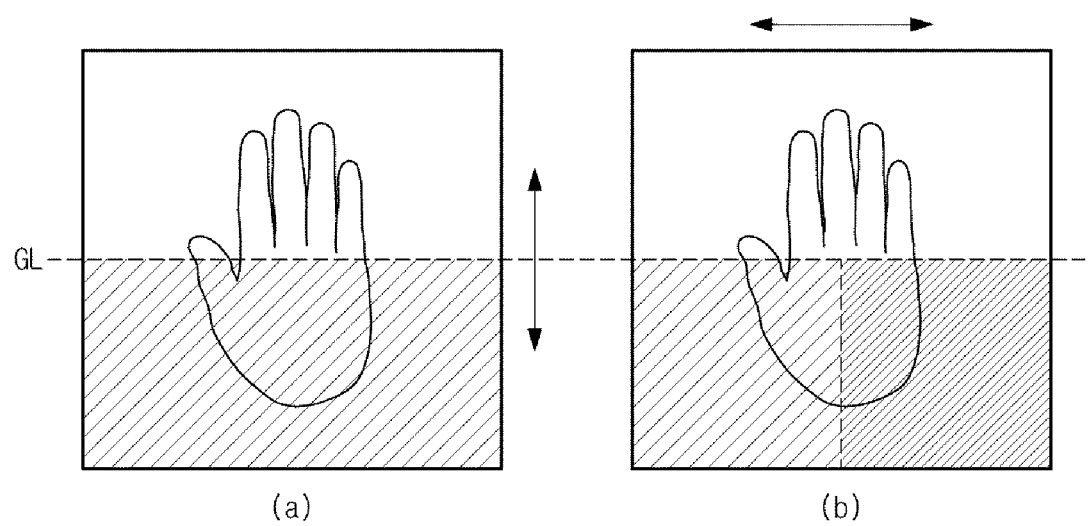
FIG. 5 shows X-ray images created by a general gate scan method.

FIG. 4 is a view for describing a general gate scan method of the X-ray detector 120 to detect X-rays, and FIG. 5 shows X-ray images created by the general gate scan method.

If the X-ray detector 120 detects X-rays from a certain gate line GL, as shown in FIG. 4A, the X-ray detector 120 may perform gate scanning downward from the gate line GL, and then again perform gate scanning from the first row in order to read out actual X-ray image signals, as shown in FIG. 4B. Also, in order to read out a signal of an actual X-ray image from the gate line GL from which the X-rays have been detected, the X-ray detector 120 may perform gate scanning downward from the gate line GL, and then again perform gate scanning from the first row to the gate line GL from which the X-rays have been detected, as shown in FIG. 4C. Then, the X-ray detector 120 may combine two regions on which the gate scanning has been performed, through image post-processing. Reading out X-rays means reading out data lines DL with respect to a certain gate line GL.

However, when gate scanning is performed by the general gate scan method as shown in FIG. 4, X-ray signals may be lost due to leakage and current trap during reading out to detect X-rays. Furthermore, due to a waiting time during reading out of a gate line from which X-rays have been detected, an image level difference may be made between the upper and lower regions of the gate line GL, during reading out a signal of an actual X-ray image.

Referring to FIGS. 5A and 5B, a level difference of an X-ray image is made between the upper and lower regions of a gate line GL from which X-rays have been detected, and also due to leakage and current trap, a level difference is made between the left and right regions of the X-ray image.

In order to reduce a level difference of an image, the X-ray detector 120 may perform fast scanning or binning scanning for reducing a waiting time due to readout with respect to a region of interest, during operation of detecting X-rays. The region of interest is a region within a range of reference lines in which signal loss and an image level difference can be reduced. The region of interest may be automatically set by the X-ray detector 120, based on a gate line GL from which X-rays have been detected, or the region of interest may have been set in advance manually by a user or a manufacturer. Herein, the user is a person who diagnoses an object using the X-ray imaging apparatus 100, and may be medical personnel including a doctor, a radiological technologist, and a nurse. However, the user may be anyone who uses the X-ray imaging apparatus 100. A method of setting reference lines automatically or manually will be described later.

The binning scanning is performing pixel binning on a predetermined region of an X-ray image to acquire a low-resolution X-ray image, in order to improve the noise characteristics and image acquisition velocity/frame rate of an X-ray image when the X-ray detector 120 acquires an X-ray image. The structure and operations of the X-ray detector 120 for the binning scanning will be described later.

The image processor 130 may reconstruct a high-resolution X-ray image using a plurality of low-resolution X-ray images acquired by the X-ray detector 120. This operation will be also described later.

Figure 6:
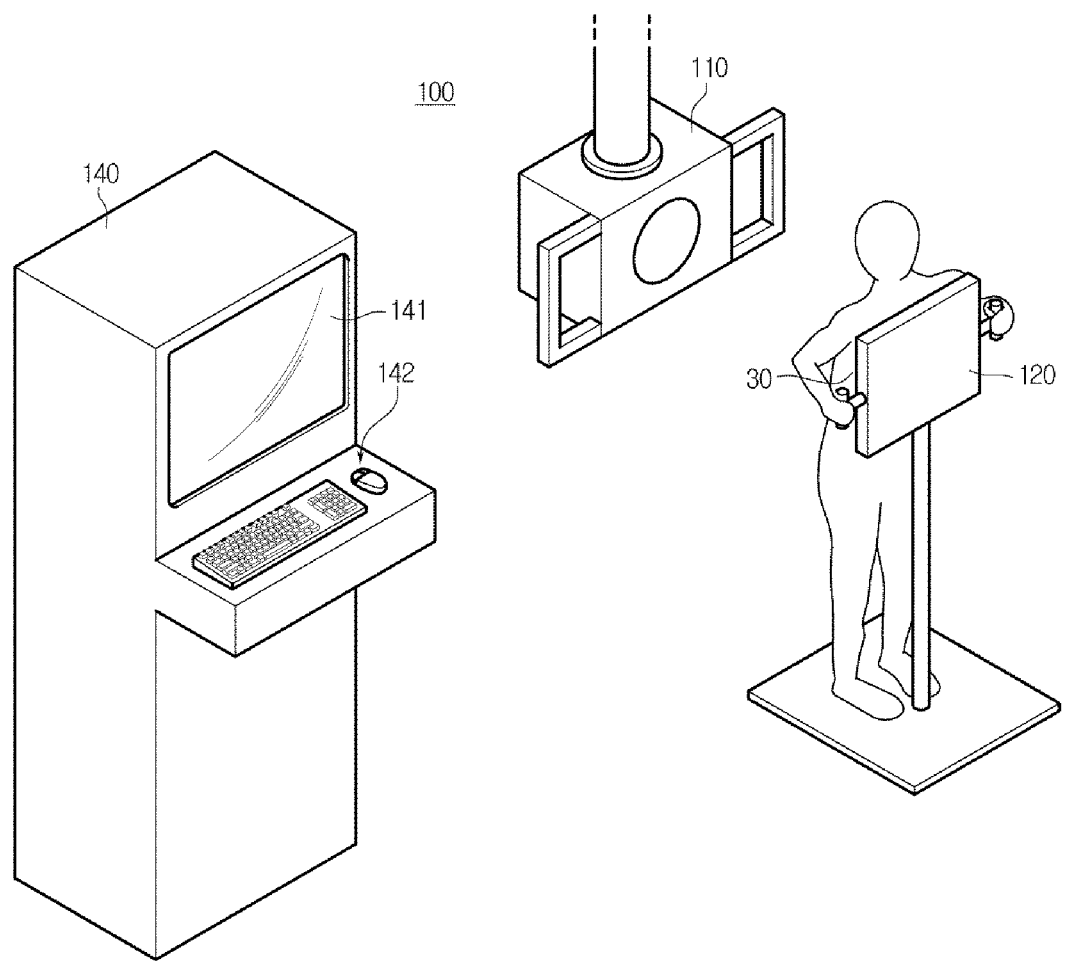
FIG. 6 shows an external appearance of an X-ray imaging apparatus for general radiography, according to an embodiment of the present disclosure.
Figure 7:
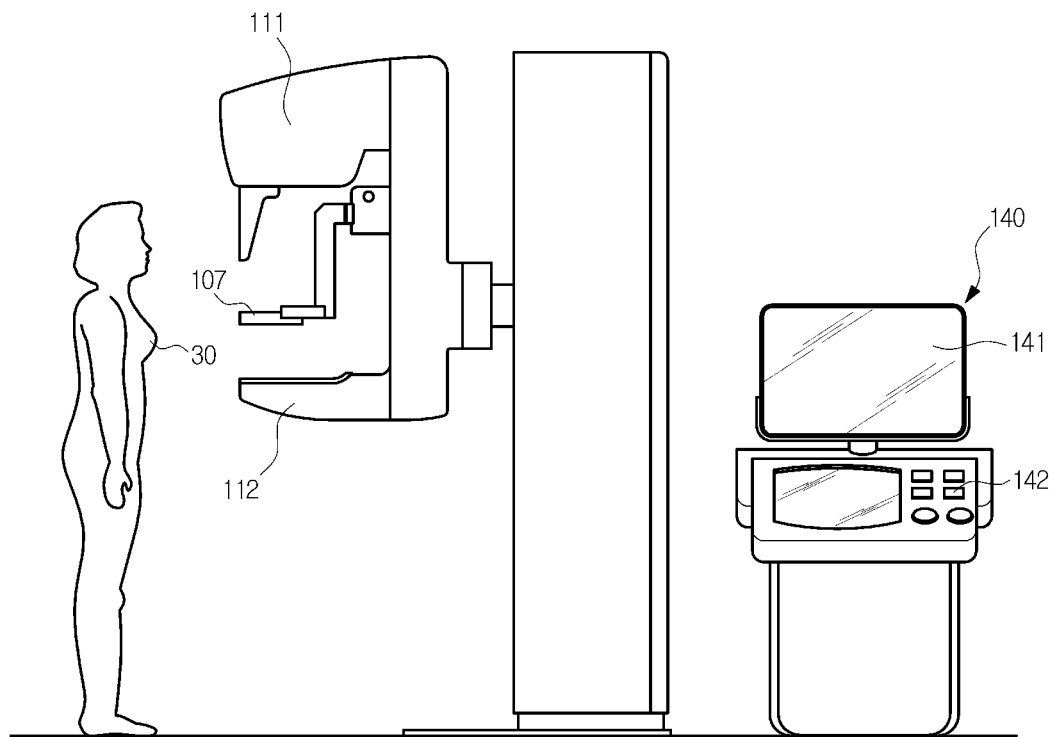
FIG. 7 shows an external appearance of an X-ray imaging apparatus for mammography, according to an embodiment of the present disclosure.
Figure 8:
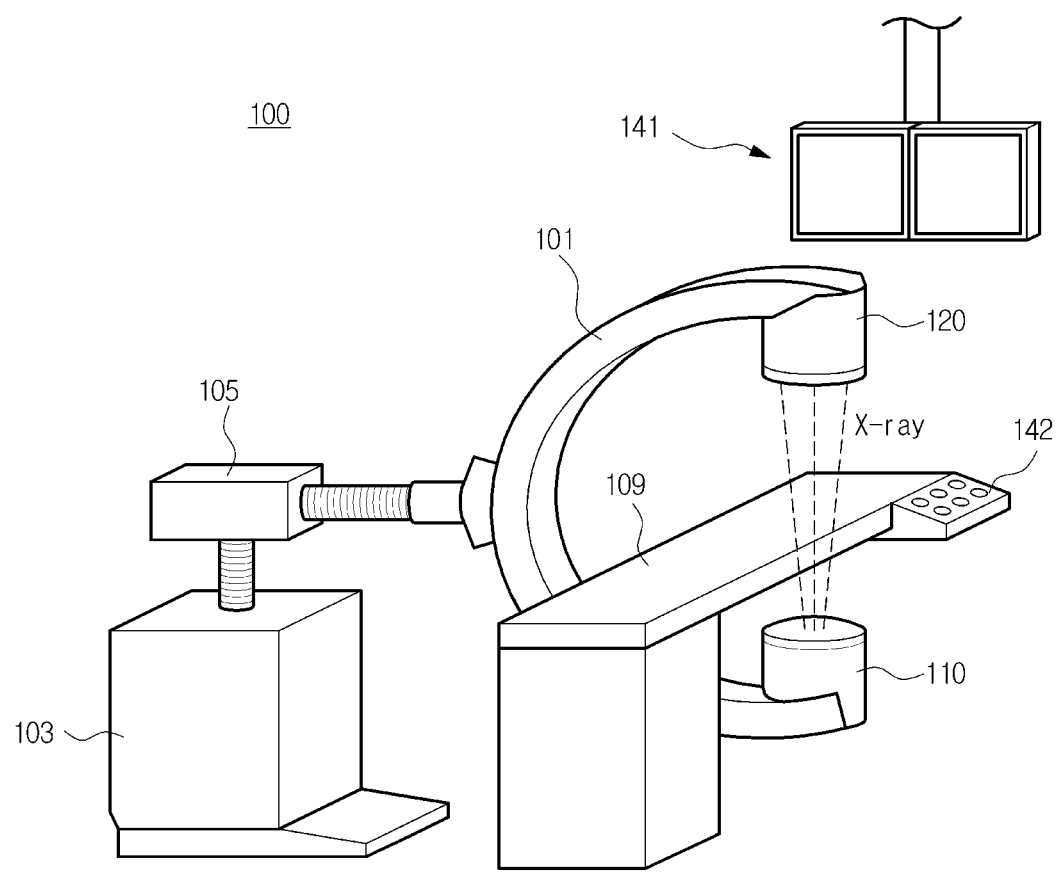
FIG. 8 shows an external appearance of an X-ray imaging apparatus for photographing real-time moving images, according to an embodiment of the present disclosure.

FIG. 6 shows an external appearance of an X-ray imaging apparatus for general radiography, according to an embodiment of the present disclosure, FIG. 7 shows an external appearance of an X-ray imaging apparatus for mammography, according to an embodiment of the present disclosure, and FIG. 8 shows an external appearance of an X-ray imaging apparatus for photographing real-time moving images, according to an embodiment of the present disclosure.

As shown in FIG. 6, the X-ray imaging apparatus 100 according to an embodiment of the present disclosure may be applied to perform general radiography.

The X-ray source 110 may be connected to the ceiling of a radiation room such that the height of the X-ray source 110 can be adjusted. If the X-ray source 110 is implemented as a sealing type, the X-ray source 110 may move in forward/backward and left/right directions along a guide rail provided on the ceiling of the radiation room.

An object 30 may be placed between the X-ray source 110 and the X-ray detector 120. The object 30 may be the chest, arms, legs, etc.

Meanwhile, in FIG. 6, the X-ray detector 120 is a stand type, however, the X-ray detector 120 is not limited to a stand type. For example, the X-ray detector 120 may be a portable type.

The X-ray imaging apparatus 100 may further include a host unit 140 that provides a user interface. The host unit 140 is also called a workstation. The host unit 140 may include a display unit 142 to display information for control operations of the X-ray imaging apparatus 100 or created X-ray images, and an input unit 141 to receive instructions from a user.

Meanwhile, the image processor 130 (see FIG. 1) may be also included in the host unit 140, however, the embodiment of the X-ray imaging apparatus 100 is not limited to this. That is, the image processor 130 may be included in any other unit according to another embodiment of the X-ray imaging apparatus 100.

Also, as shown in FIG. 7, the X-ray imaging apparatus 100 according to an embodiment of the present disclosure may be applied to perform mammography. In this case, likewise, a breast which is an object 30 may be placed between the X-ray source 110 and the X-ray detector 120. The X-ray imaging apparatus 100 may further include a pressure paddle 107 for pressing a breast in a vertical direction, between the X-ray source 110 and the X-ray detector 120.

The X-ray imaging apparatus 100 for mammography may also include the host unit 140 so that a user can adjust a location of the pressure paddle 107 through the input unit 141 of the host unit 140.

Also, the X-ray imaging apparatus 100 may perform fluoroscopy to photograph real-time X-ray moving images. For example, the X-ray imaging apparatus 100 may have a C-arm 101 as shown in FIG. 8. The X-ray source 110 and the X-ray detector 120 may be respectively installed at both ends of the C-arm 101. The C-arm 101 may be connected to a main body 103 through a connection shaft 105, and may rotate in an orbital direction.

A patient table 109 may be placed between the X-ray source 110 and the X-ray detector 120. If an object is positioned on the patient table 109, the X-ray source 110 may irradiate X-rays on the object, and the X-ray detector 120 may detect X-rays transmitted through the object to acquire an X-ray image of the object.

The X-ray imaging apparatus 100 can acquire real-time X-ray moving images about the object. A user can input various control instructions for radiography through the input unit 141, and perform a procedure or diagnosis such as angiography while viewing the display unit 142 including a plurality of screens that display various images for the procedure or diagnosis.

Figure 9:
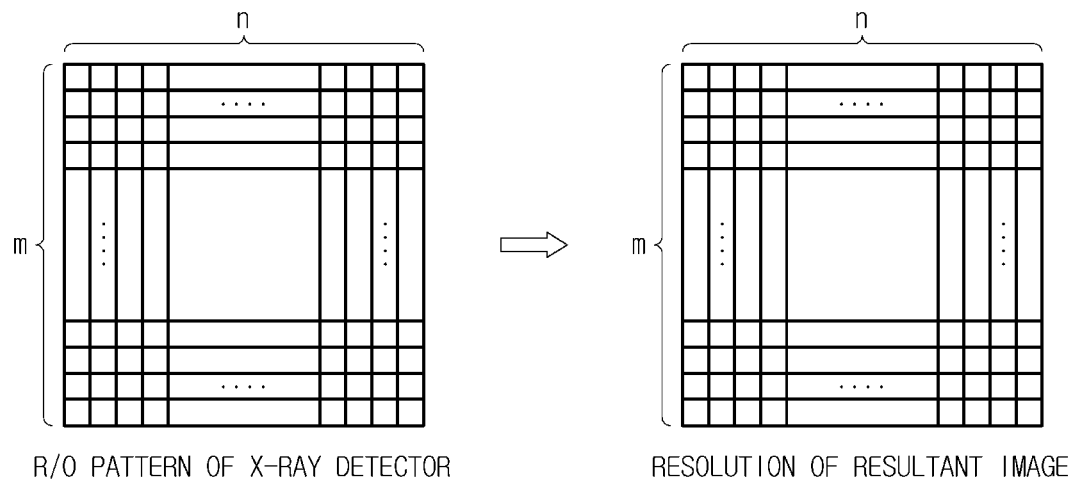
FIG. 9 is a view for describing a general method of producing X-ray images.
Figure 10:
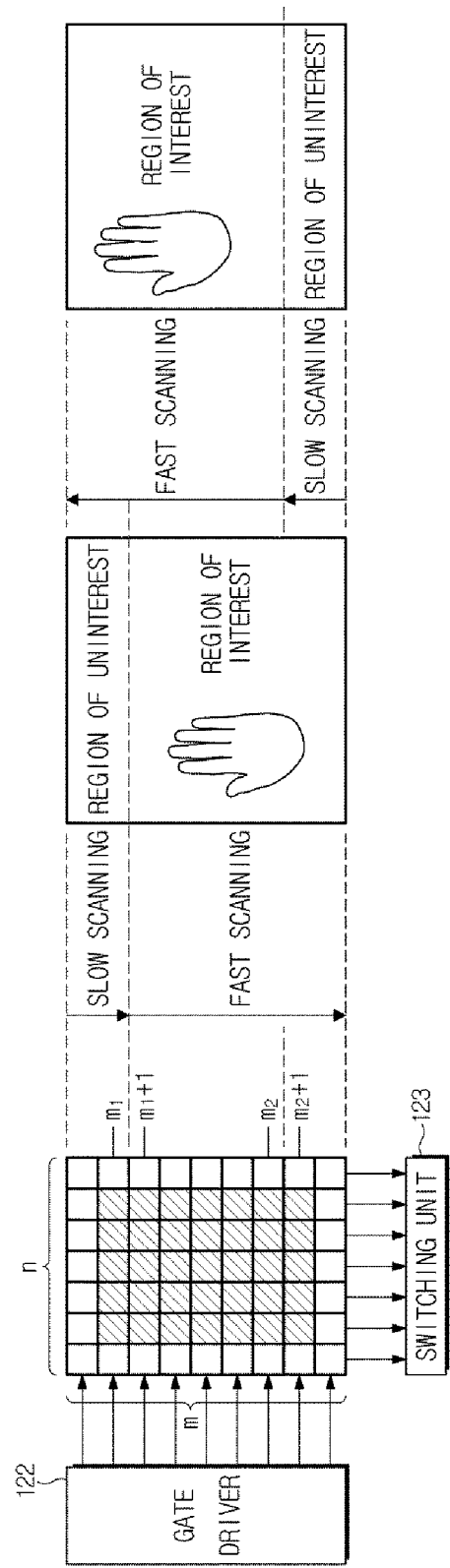
FIGS. 10 and 11 are views for describing a gate scan method of an X-ray detector according to an embodiment of the present disclosure.
Figure 11:
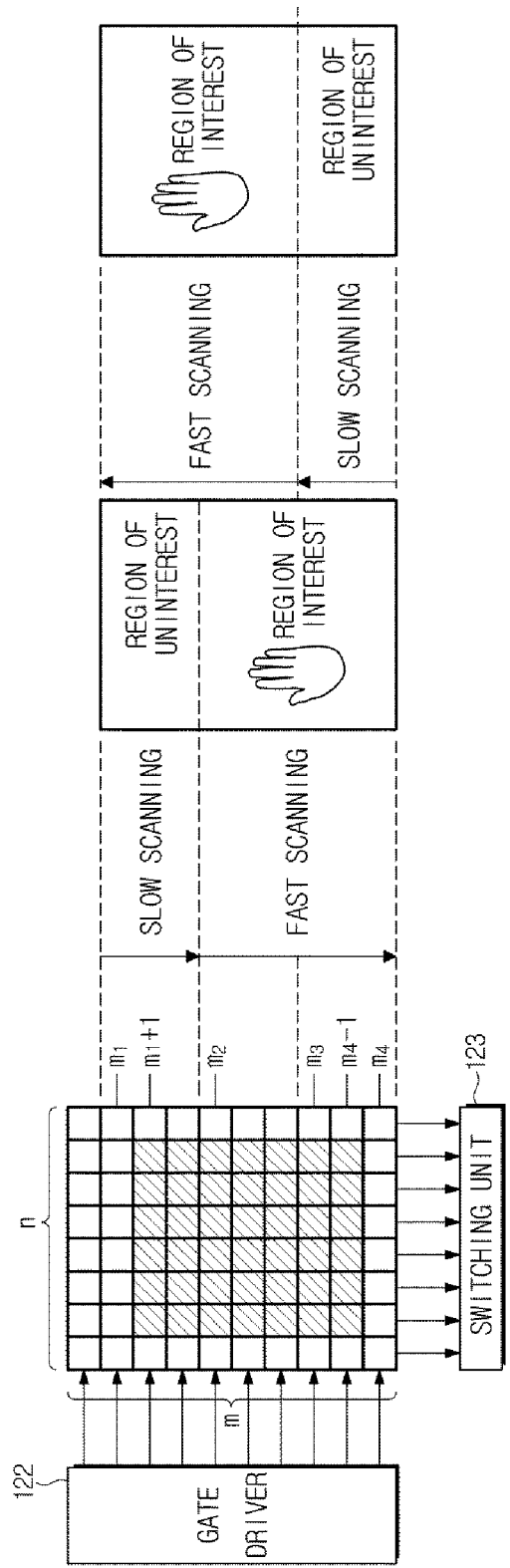

FIG. 9 is a view for describing a general method of producing X-ray images, and FIGS. 10 and 11 are views for describing a gate scan method of the X-ray detector 120 according to an embodiment of the present disclosure.

Referring to FIG. 9, if the X-ray detector 120 is implemented as a 2Dimensional (2D) pixel array of m×n pixels, the gate driver 122 (see FIG. 3) may apply a gate signal sequentially to m rows or m gate lines GL, and signals may be read out from the n pixels or n data lines DL of each row or each gate line GL. The following description will be given based on rows and pixels. The X-ray detector 120 can use a signal read out from each pixel as a pixel value to create a high-resolution X-ray image with m×n resolution and to detect X-rays from the pixel.

Meanwhile, referring to FIG. 10, the gate driver 122 of the X-ray detector 120 according to an embodiment of the present disclosure may apply a turn-on signal for driving each transistor 121c, to the first to m-th rows, sequentially, in order to detect X-rays from an X-ray detection region. If X-rays are detected from a certain row (for example, the m1-th row), the gate driver 122 may reduce a turn-on time period of the turn-on signal from the lower row (that is, the (m1+1)-th row). Also, the gate driver 122 of the X-ray detector 120 may apply a turn-on signal for driving each transistor 121c, to the m-th to first rows, in reverse order, in order to detect X-rays from the X-ray detection region. If X-rays are detected from the (m2+1)-th row, the gate driver 122 may reduce a turn-on time period of the turn-on signal from the upper row (that is, the m2-th row).

That is, the X-ray detector 120 may perform slow scanning while applying a turn-on signal to the first to m1-th rows, fast scanning while applying a turn-on signal to the (m1+1)-th to m2-th rows, and slow scanning while applying a turn-on signal to the (m2+1) to m-th rows. Slow scanning is turning on the transistors 121c of each row for a time period that is longer than or equal to a predetermined threshold time period to read out signals from the n pixels, and fast scanning is turning on the transistors 121c of each row for a time period that is shorter than the predetermined time period to read out signals from the n pixels. Scanning may be performed from the first to m-th rows, sequentially, or from the m-th to first rows, in reverse order. In the following description, a pixel region of rows on which slow scanning is performed is referred to as a region of uninterest (or no-interest), and a pixel region of rows on which fast scanning is performed is referred to as a region of interest. In the current embodiment, the (m1+1)-th row that is the lower row of the m1-th row from which X-rays have been detected is set to a first reference line, and the m2-th row that is the upper row of the (m2+1)-th row from which X-rays have been detected is set to a second reference line.

However, according to another embodiment, the first reference line and the second reference line may be set to arbitrary lines, instead of the (m1+1)-th row that is the lower row of the m1-th row from which X-rays have been detected and the m2-th row that is the upper row of the (m2+1)-th row from which X-rays have been detected. That is, the first reference line and the second reference line, which are reference rows or reference gate lines GL that divide a region to be subject to fast scanning from a region to be subject to slow scanning, may have been set in advance by a user or a manufacturer. Also, the first reference line and the second reference line may be respectively set to any lower row of the m1-th row from which X-rays have been detected and any upper row of the (m2+1)-th row from which X-rays have been detected.

Also, referring to FIGS. 3 and 11, the gate driver 122 of the X-ray detector 120 according to another embodiment may apply a turn-on signal for driving the transistors 121c to the first to m-th rows, sequentially, in order to detect X-rays from the X-ray detection region. At this time, the gate detector 120 may set a turn-on time period of a turn-on signal that is applied to the m1-th to (m2−1)-th rows to a first time period, a turn-on time period of a turn-on signal that is applied to the m2-th to (m3−1)-th rows to a second time period, and a turn-on time period of a turn-on signal that is applied to the m3-th to m4-th rows to the first time period. In this case, pixels corresponding to the m1-th to (m2−1)-th rows and the m3-th to m4-th rows may be dummy pixels, which correspond to a region of uninterest of an object. The X-ray detector 120 may set the m1-th to m4-th rows such that any one of the m1-th to (m2−1)-th rows and the m3-th to m4-th rows corresponding to the region of uninterest becomes an X-ray detection line, or the X-ray detector 120 may receive a setting of an X-ray detection line from a user through the input unit 141 (see FIG. 6, 7, or 8). Herein, the first time period may be set to a time period that is longer than or equal to 3 μs, and the second time period may be set to a time period that is shorter than 3 μs. The X-ray detection line is a gate line GL or a row from which X-rays begin to be detected.

That is, the X-ray detector 120 may be set to perform slow scanning while applying a turn-on signal to the m1-th to (m2−1)-th rows, and to perform fast scanning while applying a turn-on signal to the m2-th to m4-th rows. Or, the X-ray detector 120 may be set to perform slow scanning while applying a turn-on signal to the m4-th to m3-th rows, and to perform fast scanning while applying a turn-on signal to the (m3−1)-th to m1-th rows. If X-rays are detected from any row of the m1-th to (m2−1)-th rows on which slow scanning is set to be performed, the X-ray detector 120 may perform fast scanning sequentially from the row from which the X-rays have been detected. Or, if X-rays are detected from any row of the m4-th to m3-th rows on which slow scanning is set to be performed, the X-ray detector 120 may perform fast scanning in reverse order from the row from which the X-rays have been detected. Slow scanning is for the gate driver 122 to apply a turn-on signal to a row for the first time period to read out signals from the n pixels of the row, and fast scanning is for the gate driver 122 to apply a turn-on signal to a row for the second time period to read out signals from the n pixels of the row. A pixel region of rows on which slow scanning is performed is referred to as a region of uninterest, and a pixel region of rows on which fast scanning is performed is referred to as a region of interest. In the current embodiment, it is assumed that the lower row (that is, the m2-th row) of the (m1+1)-th row from which X-rays have been detected is a third reference line, and the upper row (that is, the m3-th row) of the (m4−1)-th row from which X-rays have been detected is a fourth reference line.

Meanwhile, according to another embodiment, the third reference line and the fourth reference line may be arbitrarily set to any rows among the lower rows of the (m1+1)-th row from which X-rays have been detected or the upper rows of the (m4−1)-th row from which X-rays have been detected, instead of the next row of the (m1+1)-th row from which X-rays have been detected and the previous row of the (m4−1)-th row from which X-rays have been detected. That is, the third reference line and the fourth reference line, which are reference rows or reference gate lines GL that divide a region to be subject to fast scanning from a region to be subject to slow scanning, may have been set in advance by a user or a manufacturer. In other words, the third and fourth reference lines function as predetermined threshold lines for performing slow scanning. If the X-ray detector 120 detects no X-rays up to the third reference line (that is, the m2-th row) while performing slow scanning sequentially, the X-ray detector 120 may again perform slow scanning from the first row in order to detect X-rays after fast scanning. If the X-ray detector 120 detects no X-rays up to the fourth reference line (that is, the m3-th row) while performing slow scanning in reverse order, the X-ray detector 120 may again perform slow scanning from the m-th row in order to detect X-rays after fast scanning.

Figure 12:
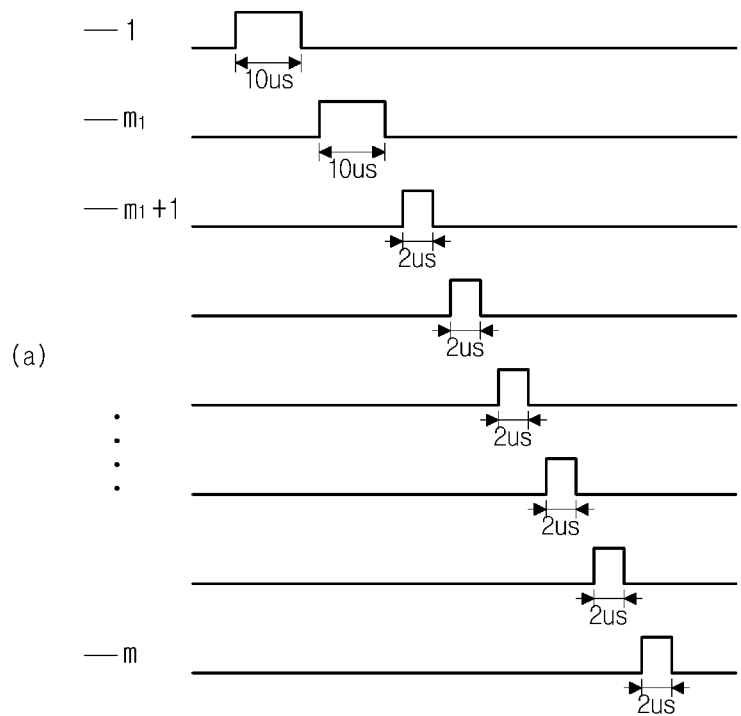
FIG. 12 is a timing diagram of turn-on signals that are applied to the individual rows of the X-ray detector of FIG. 10.
Figure 12:
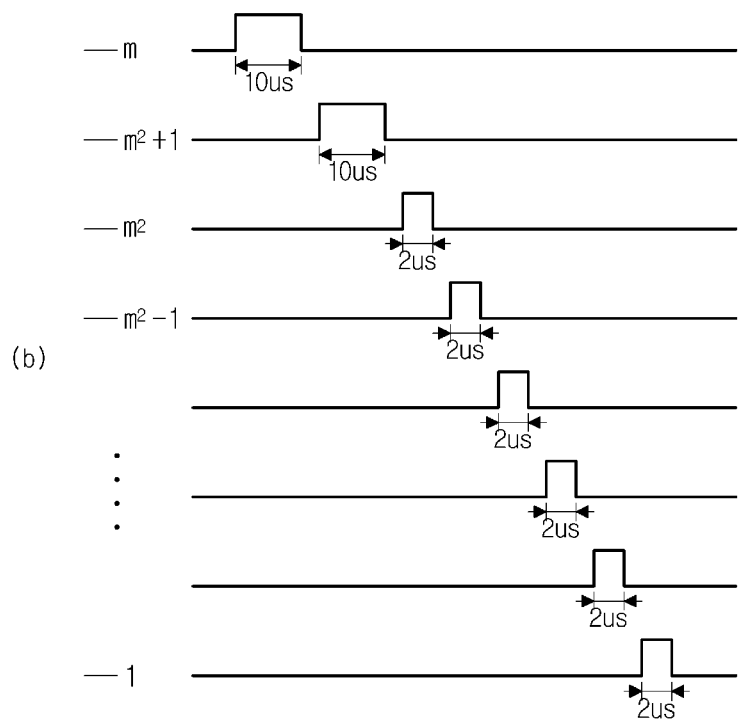

FIG. 12 is a timing diagram of turn-on signals that are applied to the individual rows of the X-ray detector 120 of FIG. 10 in order to detect X-rays.

Referring to FIG. 12A, a turn-on signal that is applied to the first to m1-th rows may be sequentially turned on for a time period of 10 μs, and a turn-on signal that is applied to the (m1+1)-th to m2-th rows may be sequentially turned on for a time period of 2 μs. Or, referring to FIG. 12B, a turn-on signal that is applied to the m-th to (m2+1)-th rows may be turned on in reverse order for a time period of 10 μs, and a turn-on signal that is applied to the m2-th to first rows may be turned on in reverse time for a time period of 2 μs. Herein, the m1-th row and the m2-th row are X-ray detection lines.

Thereafter, if X-rays are detected, and a predetermined window time period elapses, the X-ray detector 120 may again apply a turn-on signal to the first to m-th rows in order to read out signals of an actual X-ray image. The turn-on signal that is applied to read out signals of an actual X-ray image needs to have a turn-on time period that is longer than or equal to a predetermined time period in order to extract X-rays, unlike when fast scanning is performed. The turn-on time period of the turn-on signal may be 10 μs.

That is, the X-ray detector 120 may perform i) X-ray detection operation of determining whether X-rays have been irradiated from the X-ray source 110, and ii) readout operation of reading out actual X-ray image signals after a predetermined window time period has elapsed. Slow scanning and fast scanning are performed in the X-ray detection operation.

As such, by performing slow scanning to detect X-rays, and performing fast scanning on pixels after a row from which X-rays have been detected, a waiting time due to readout may be reduced, and a level difference of an X-ray image can be reduced when signals of an actual X-ray image are again read out, due to uniform fast scanning performed on a region of interest from the (m1+1)-th to m2-th rows.

Figure 13:
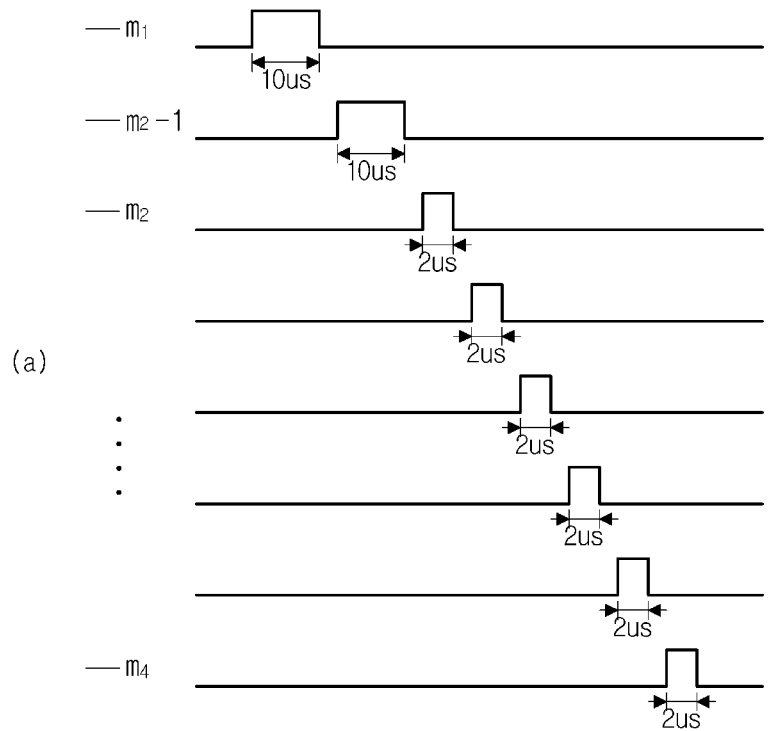
FIG. 13 is a timing diagram of turn-on signals that are applied to the individual rows of the X-ray detector of FIG. 11.
Figure 13:
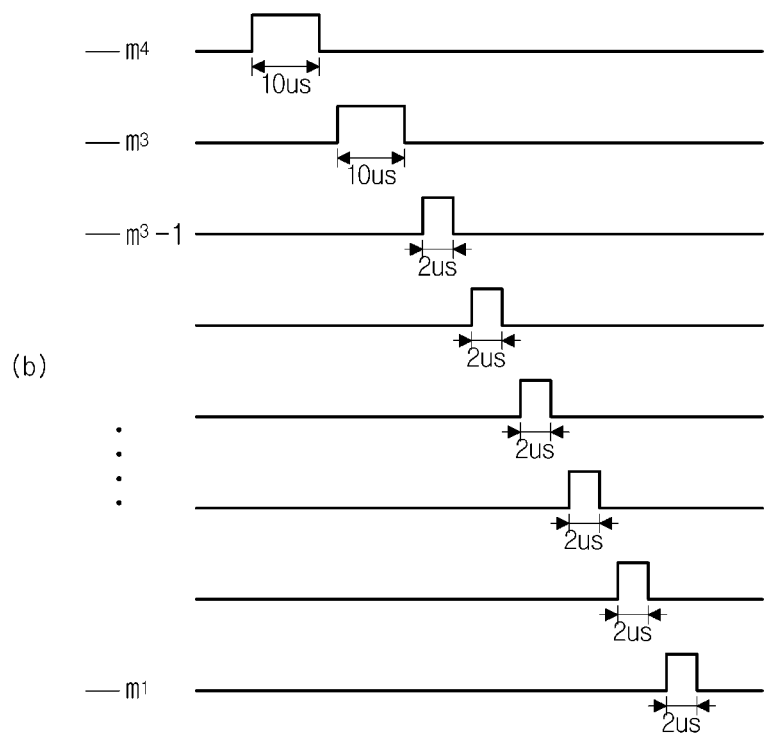

FIG. 13 is a timing diagram of turn-on signals that are applied to the individual rows of the X-ray detector 120 of FIG. 11.

Referring to FIG. 13A, a turn-on signal that is applied to the m1-th to (m2−1)-th rows may be turned on sequentially for a time period of 10 μs, and a turn-on signal that is applied to the m2-th to m4-th rows may be turned on sequentially for a time period of 2 μs. Also, referring to FIG. 13B, a turn-on signal that is applied to the m4-th to m3-th rows may be turned on in reverse order for a time period of 10 μs, and a turn-on signal that is applied to the (m3−1)-th to m1-th rows may be turned on in reverse order for a time period of 2 μs.

As such, by performing fast scanning on pixels of the m2-th to m4-th rows or pixels of the (m3−1)-th to m1-th rows, which correspond to a region of interest, in the X-ray detection operation, a waiting time due to readout may be reduced, and a level difference of an X-ray image can be reduced when signals of an actual X-ray image are again read out, due to uniform fast scanning performed on the region of interest from the m2-th to (m3−1)-th rows.

Figure 14:
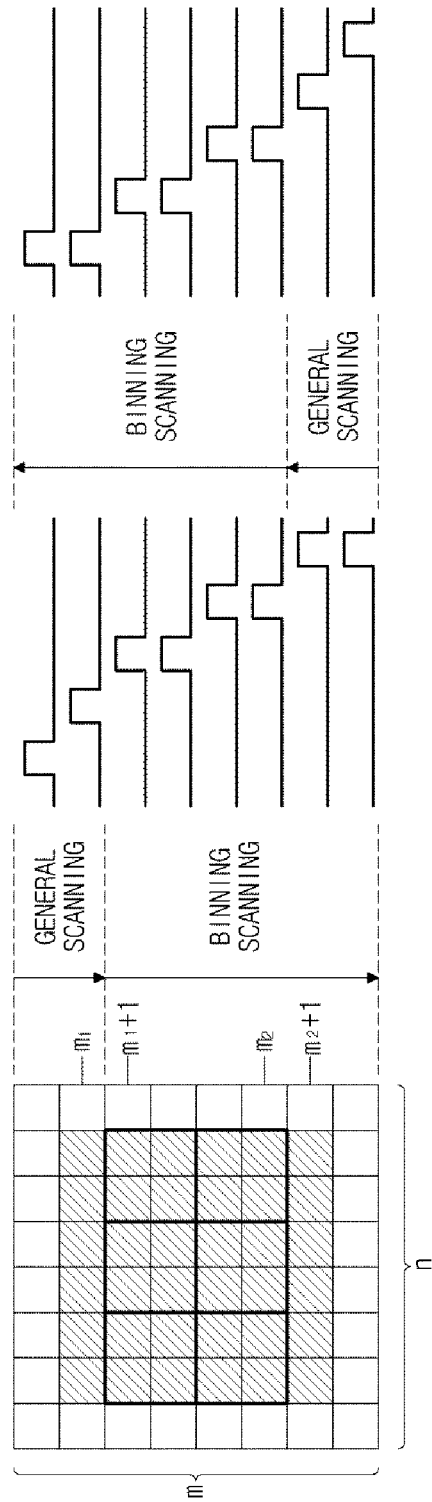
FIGS. 14 and 15 are views for describing an X-ray detection method of an X-ray detector according to another embodiment of the present disclosure.
Figure 15:
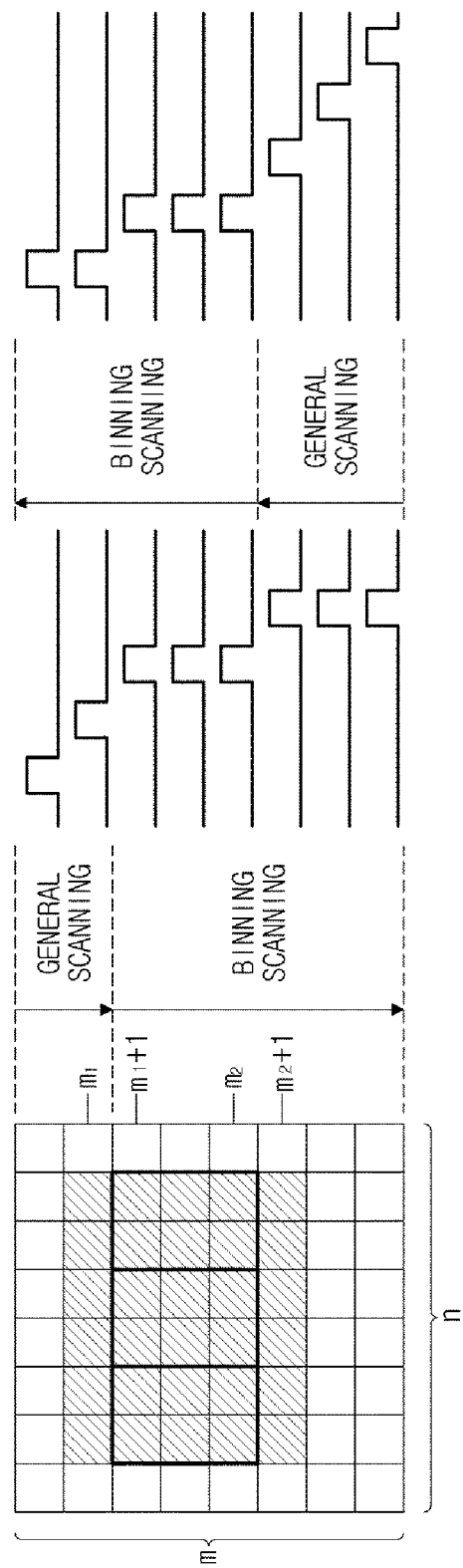

FIGS. 14 and 15 are views for describing an X-ray detection method of the X-ray detector 120 according to another embodiment of the present disclosure.

Referring to FIGS. 3, 14, and 15, the gate driver 122 of the X-ray detector 120 according to another embodiment of the present disclosure may apply a turn-on signal for driving the transistors 121c to the first to m-th rows, sequentially. If X-rays are detected from a row (for example, the m1-th row) of the rows, the X-ray detector 120 may synchronize a turn-on time of a turn-on signal from the lower row (that is, the (m1+1)-th row). Meanwhile, the gate driver 122 of the X-ray detector 120 may apply a turn-on signal for driving the transistors 121c to the m-th to first rows, in reverse order, and if X-rays are detected from a row (for example, the (m2+1)-th row) of the rows, the X-ray detector 120 may synchronize a turn-on time of a turn-on signal from the upper row (that is, the m2-th row).

Referring to FIG. 14, the gate driver 122 of the X-ray detector 120 according to an embodiment of the present disclosure may perform 2×2 binning scanning in order to synchronize a turn-on time of a turn-on signal that is applied to the (m1+1)-th to m-th rows or to the m2-th to first rows. Referring to FIG. 15, the gate driver 122 may perform 3×2 binning scanning. Operations of the X-ray detector 120 related to binning scanning will be described later.

Meanwhile, the gate driver 122 of the X-ray detector 120 according to another embodiment that divides scanning lines based on the third and fourth reference lines, as shown in FIG. 11, may apply a turn-on signal to the first to m-th rows, sequentially, in such a manner to apply a turn-on signal to the m1-th to (m2−1)-th rows, sequentially, and to apply turn-on signals having a synchronized turn-on time to the m2-th to (m3−1)-th rows. Also, the gate driver 122 may apply a turn-on signal to the m-th to first rows, in such a manner to apply a turn-on signal to the m4-th to m3-th rows, in reverse order, and to apply turn-on signals having a synchronized turn-on time to the (m3−1)-th to the m1-th rows. In this case, pixels corresponding to the m1-th to (m2−1)-th rows and to the m3-th to m4-th rows are dummy pixels, which correspond to a region of uninterest of an object. The X-ray detector 120 may set the m1-th to m4-th rows such that any one row of the m1 to (m2−1)-th rows and the m3-th to m4-th rows, which correspond to the region of uninterest, becomes an X-ray detection line. That is, the X-ray detector 120 may be set to perform general scanning sequentially while applying a turn-on signal to the m1-th to (m2−1)-th rows, and to perform binning scanning while applying a turn-on signal to the m2-th to m4-th rows. Or, the X-ray detector 120 may be set to perform general scanning in reverse order while applying a turn-on signal to the m4-th to m3-th rows, and to perform binning scanning while applying a turn-on signal to the (m3−1)-th to m1-th rows. If X-rays are detected from any one row of the m1-th to (m2−1)-th rows on which general scanning is set to be performed, the X-ray detector 120 may perform binning scanning after the row from which X-rays have been detected. If X-rays are detected from any one row of the m4-th to m3-th rows on which general scanning is set to be performed in reverse order, the X-ray detector 120 may perform binning scanning after the row from which X-rays have been detected.

Synchronizing a turn-on time is for the X-ray detector 120 to perform binning scanning. The binning scanning is a method of combining a plurality of adjacent pixels to receive signals in order to improve a frame rate and noise characteristics and to perform radiography with a low dose. Hereinafter, binning scanning will be described in detail with reference to FIG. 16.

Figure 16:
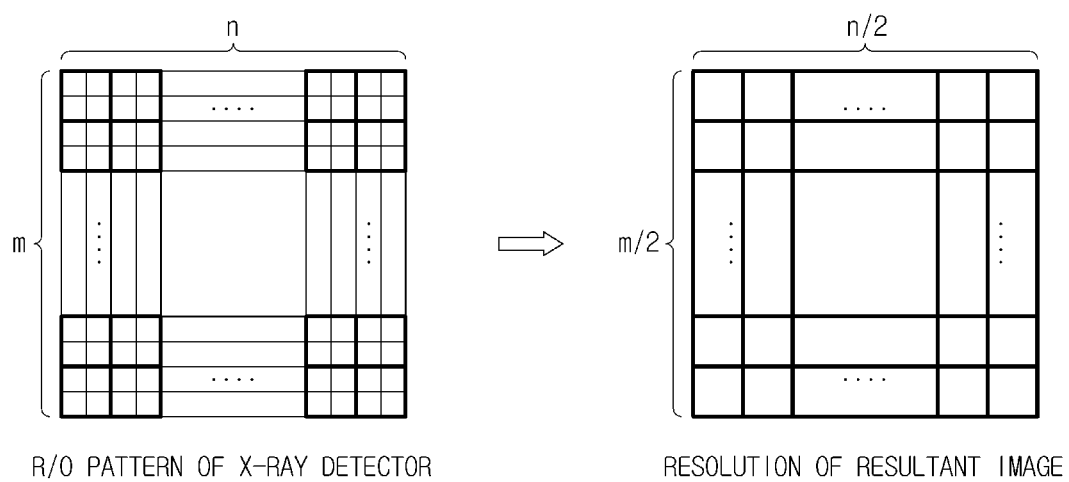
FIG. 16 shows an example of super pixels acquired when binning scanning is performed.
Figure 17:
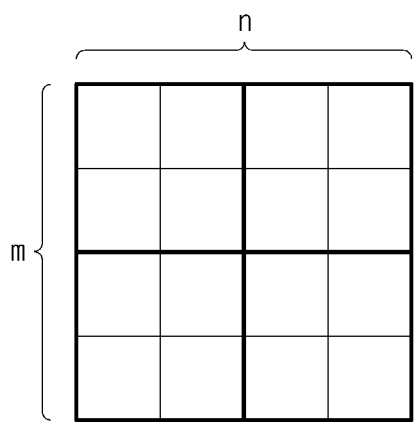
FIG. 17 shows two examples of binning patterns for 2×2 binning scanning.
Figure 17:
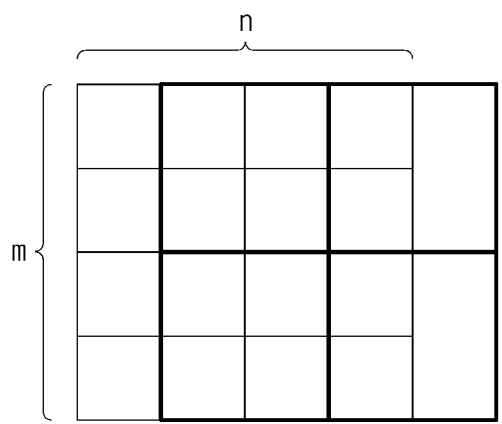

FIG. 16 shows an example of super pixels acquired when binning scanning is performed, and FIG. 17 shows two examples of binning patterns for 2×2 binning scanning. Locations of individual pixels on the X-ray detector 120 can be represented as 2D coordinates (rows and columns).

For example, when 2×2 binning scanning is performed, as shown in FIG. 16, 2×2 adjacent pixels are combined to read out signals. At this time, the 2×2 adjacent pixels function as a super pixel so that the resultant image has resolution of m/2×n/2.

The binning scanning may be performed on an X-ray detection region to combine charges, may be performed on a readout circuit to combine charges or analog signals, or may be performed after signals passed through an ADC to combine digital signals. If pixel binning is performed, spatial resolution of an X-ray image may deteriorate although Signal to Noise Ratio (SNR) or temporal resolution of the X-ray image is improved.

When the X-ray detector 120 performs 2×2 pixel binning, as shown in FIG. 17A, the X-ray detector 120 may group pixels at locations of (1,1), (1,2), (2,1), and (2,2) into a super pixel, and group the remaining pixels into super pixels by grouping four adjacent pixels into a super pixel.

Also, as shown in FIG. 17B, the X-ray detector 120 may group pixels at locations of (1,2), (1,3), (2,2), and (2,3) into a super pixel. The 2×2 binning scanning as shown in FIG. 16 is an example of binning scanning that is performed by the X-ray imaging apparatus 100. As another example, the X-ray imaging apparatus 100 may perform 3×2 binning scanning as shown in FIG. 15. If a combination of pixels constituting a super pixel is referred to as a binning set, a size of a binning set may be adjusted in consideration of the properties of an object, a purpose of radiography, etc.

Meanwhile, in embodiments that will be described below, an X-ray image that is acquired by the X-ray detector 120 is signals (that is, raw data) output from the readout circuit 124, and an X-ray image that is created by the image processor 130 is an image resulting from applying image processing such as image reconstruction to the raw data.

Also, the terms "low resolution" and "high resolution" are relative concepts. The "low resolution" represents resolution that is lower than the resolution of the X-ray detector 120, and the "high resolution" represents the resolution of the X-ray detector 120 or resolution that is higher than the resolution of the X-ray detector 120.

Hereinafter, the X-ray detector 120 that divides scanning lines based on the first and second reference lines as shown in FIG. 10 to divide a region of uninterest from a region of interest and performs 2×2 binning scanning will be described as an example. However, the X-ray detector 120 may divide scanning lines based on the third and fourth reference lines as shown in FIG. 11 and perform binning scanning with binning sets having different sizes.

Referring again to FIG. 14, the gate driver 122 of the X-ray detector 120 according to an embodiment of the present disclosure may apply a turn-on signal sequentially to the first to m1-th rows and the (m2+1)-th to m-th rows, which correspond to regions of uninterest, according to a binning pattern shown in FIG. 17A, to perform general scanning, and may apply a turn-on signal to the (m1+1)-th to m-th rows, which correspond to a region of interest, according to a binning scanning process. For example, when 2×2 binning scanning is performed on a region of interest, turn-on signals may be simultaneously applied to the transistors 112c of the (m1+1)-th and (m1+2)-th rows since (m1+1, 1), (m1+1, 2), (m1+2, 1), and (m1+2, 2) form a super pixel. That is, turn-on signals may be simultaneously applied to the gate lines GL1 of the (m1+1)-th and (m1+2)-th rows. All the remaining pixels may be grouped into super pixels by grouping four adjacent pixels into a super pixel, and turn-on signals may be simultaneously applied to pixels included in each super pixel. The above-described method can be applied to the case in which general scanning is performed on the m-th to (m2+1)-th rows and binning scanning is performed on the m2-th to first rows in reverse order.

Also, the gate driver 122 of the X-ray detector 120 according to an embodiment of the present disclosure may apply a turn-on signal sequentially to the first to m1-th rows, which correspond to a region of uninterest, according to a binning pattern shown in FIG. 17B, to perform general scanning, and may apply turn-on signals to the (m1+1)-th to m-th rows, which correspond to a region of interest, according to binning scanning. For example, when 2×2 binning scanning is performed on a region of interest, turn-on signals may be simultaneously applied to the transistors 112c of the (m1+1)-th and (m1+2)-th rows since (m1+1, 2), (m1+1, 3), (m1+2, 2), and (m1+2, 3) form a super pixel. That is, turn-on signals may be simultaneously applied to the gate lines GL1 of the (m1+1)-th and (m1+2)-th rows. The remaining pixels may be grouped into super pixels by grouping four adjacent pixels into a super pixel, and turn-on signals may be simultaneously applied to pixels included in each super pixel. The above-described method can be applied to the case in which general scanning is performed on the m-th to (m2+1)-th rows, and binning scanning is performed on the m2-th to first rows, in reverse order.

The 2×2 binning scanning is an example of binning scanning that is performed by the X-ray imaging apparatus 100, and a size of a binning set can be adjusted in consideration of the properties of an object, a purpose of radiography, etc.

The image processor 130 (see FIG. 1) may reconstruct a high-resolution X-ray image using a plurality of low-resolution X-ray images acquired by the X-ray detector 120. Details about an image reconstruction method will be described later.

Meanwhile, a frame time FT that is a time taken to acquire an X-ray image may be decided according to a line time LT for which a turn-on signal is applied to each line and the number m of lines. Herein, a line means a row. Accordingly, a frame time of a region of interest on which binning scanning is performed is shorter than a frame time of a region of uninterest on which no binning scanning is performed. Therefore, when X-ray moving images are acquired, a frame rate of a region of interest can be improved.

Referring again to FIG. 3, the X-ray detector 120 may include the switching unit 123 to connect the detection region 121 to the readout circuit 124. The switching unit 123 functions to combine signals output from a plurality of data lines into a single signal. Hereinafter, the structure and operations of the switching unit 123 will be described in detail.

Figure 18:
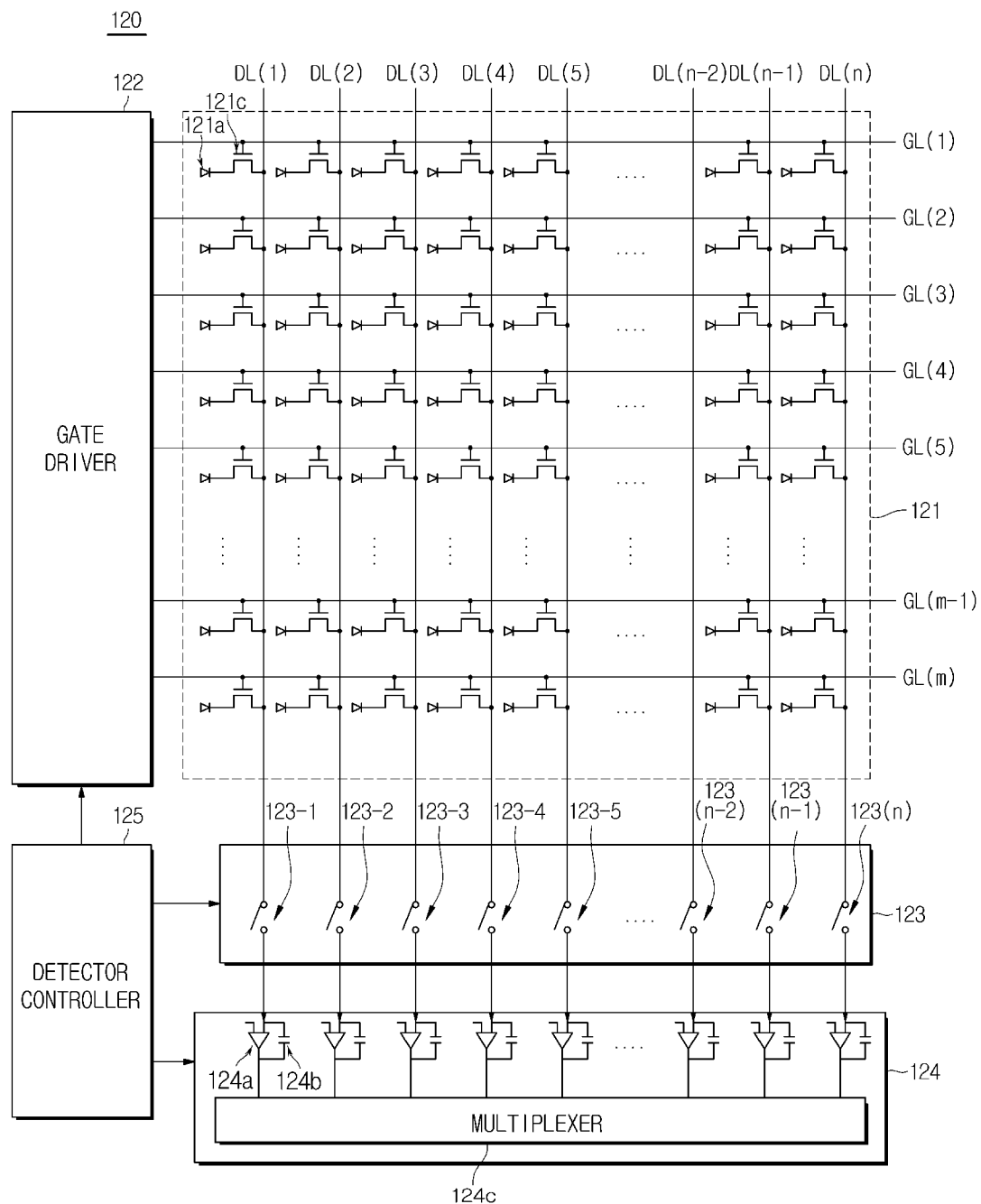
FIG. 18 shows a structure of an X-ray detector according to an example.
Figure 19:
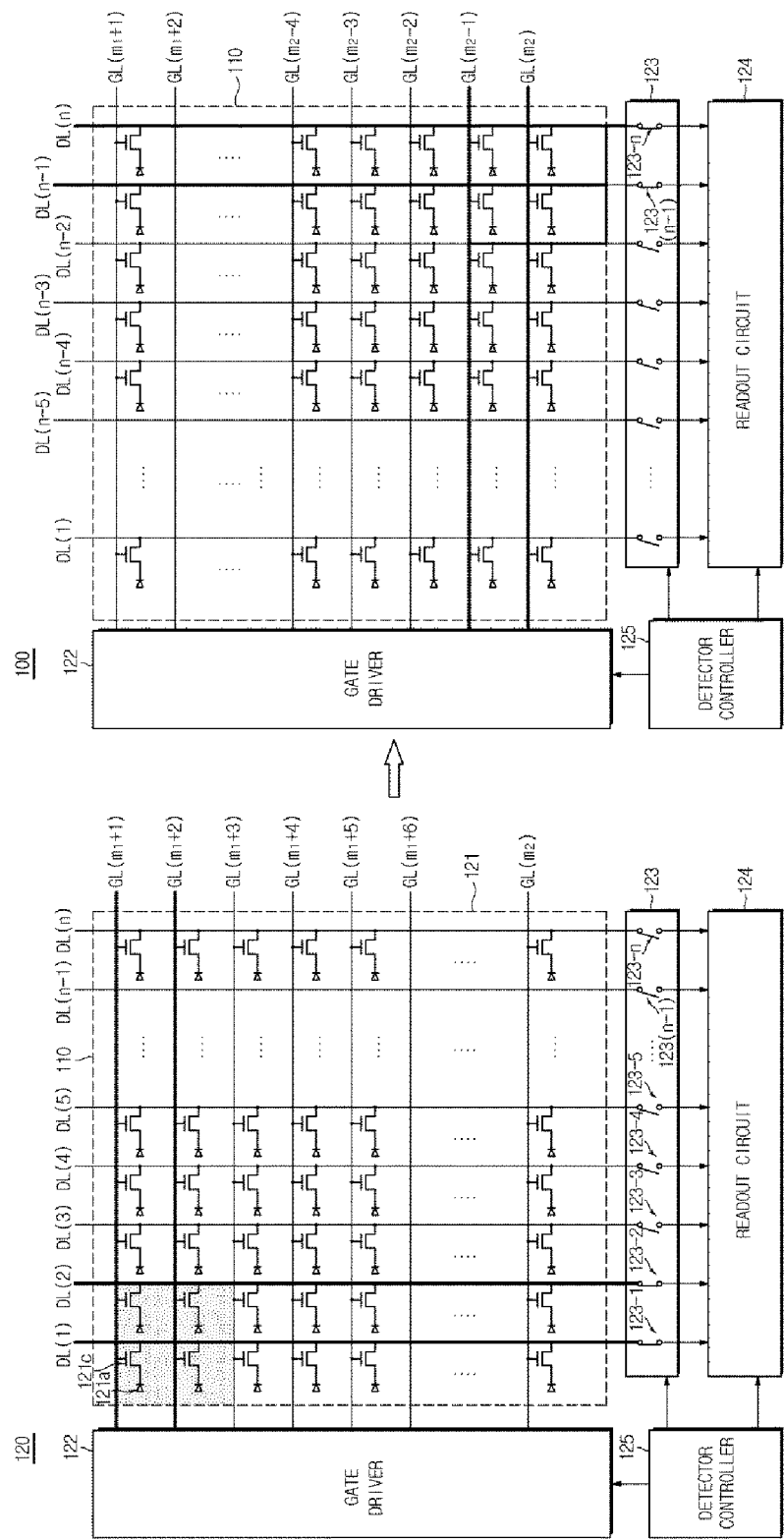
FIG. 19 is a view for describing operations of an X-ray detector according to an example.

FIG. 18 shows a structure of an X-ray detector according to an example, and FIG. 19 is a view for describing operations of an X-ray detector according to an example.

Referring to FIG. 18, electrical signals transferred through n data lines DL(1), DL(2), ..., DL(n) may be input to the readout circuit 124, and one ends of the data lines DL(1), DL(2), . . . , DL(n) may be connected to the switching unit 123 to connect the data lines DL(1),DL(2), . . . , DL(n) to the readout circuit 124.

In order to connect the data lines DL(1), DL(2), . . . , DL(n) to the readout circuit 124, the switching unit 123 may include n switching devices 123-1, 123-2, . . . , 123-$n$ corresponding to the n data lines, as shown in FIG. 18. The switching devices 123-1, 123-2, . . . , 123-$n$ may be contactless switches using semiconductor devices, such as transistors or thyristors, or mechanical switches having contacts, such as relays.

The readout circuit 124 may include n amplifiers 124*a* corresponding to the n data lines DL(1), DL(2), . . . , DL(n), and capacitors 124*b* connected to the input and output terminals of the respective amplifiers 124*a*. Also, both terminals of each capacitor 124*b* may be connected to a switch to discharge a voltage charged in the capacitor 124*b*, which is not shown in FIG. 18.

Each amplifier 124*a* may include a first input terminal connected to the switching unit 123, a second input terminal to which a reference voltage Vref is applied, and an output terminal. For example, the first input terminal may be a minus (−) terminal of the amplifier 124*a*, and the second input terminal may be a plus (+) terminal of the amplifier 124*a*.

The output terminal of the amplifier 124*a* may be connected to a multiplexer 124*c*. However, the X-ray detector 120 may include no multiplexer, and may output signals of the individual columns in parallel.

Electrical signals output from the amplifiers 124*a* may be input to the multiplexer 124*c*, and the multiplexer 124*c* may transfer the electrical signals to the image processor 130, sequentially. In order to transfer the electrical signals to the image processor 130 sequentially, the multiplexer 124*c* may be implemented as a n-to-1 multiplexer (MUX) with switches corresponding to the respective amplifiers 124*a*

The detector controller 125 may control the gate driver 122, the switching unit 123, and the readout circuit 124.

Referring to the example of FIG. 17A, in order to acquire signals from pixels located on the first and second rows, turn-on signals may be simultaneously applied to the gate line GL(1) of the first row and the gate line GL(2) of the second line (the gate lines GL(1) and GL(2) to which the turn-on signals are simultaneously applied are represented by thick lines in FIG. 19), and signals are acquired from the first data line DL(1) to the n-th data line DL(n) while the turn-on signals are applied.

As shown in FIG. 19, in order to acquire signals from a super pixel at a location of (m1+1, 1), by switching on the first switching device 123-1 connected to the first data line DL(1) and the second switching device 123-2 connected to the second data line DL(2) at the same time while simultaneously applying turn-on signals to the gate line GL(m1+1) of the (m1+1)-th row and the gate line GL(m1+2) of the (m1+2)-th row, signals can be simultaneously acquired from four pixels at locations of (m1+1, 1), (m1+1, 2), (m1+2, 1), and (m1+2, 2). The signals acquired from the four pixels may be input to the readout circuit 124.

Referring again to FIG. 18, if the readout circuit 124 includes the amplifiers 124*a* corresponding to the respective data lines DL, noise characteristics may be improved since signals acquired from the four pixels are input to the amplifiers 124*a*.

In order to acquire signals from a super pixel at a location of (m1+1, 3), the third switching device 123-3 connected to the third data line DL(3) may be connected to the readout circuit 124, and the fourth switching device 123-4 connected to the fourth data line DL(4) may be connected to the readout circuit 124 so that signals acquired from four pixels at locations of (m1+1, 3), (m1+1, 4), (m1+2, 3), and (m1+2, 4) are input to the readout circuit 124.

Signals acquired from four pixels from the super pixel at the location of (m1+1, 3) to a super pixel at the location of (m1+1, n−1) may be input to the readout circuit 124, in the same manner. Also, the first to n-th switching devices 123-1 to 123-$n$ may be switched on at the same time or at regular time intervals. Also, after signals of the (m1+1)-th and (m1+2)-th rows are acquired, signals of the remaining rows may be acquired by grouping two adjacent pixels into a super pixel sequentially up to the m2-th row, and a component for combining signals acquired from two data lines DL may be provided at an input terminal or an output terminal of the readout circuit 124.

Meanwhile, likewise, in the case of the binning pattern as shown in FIG. 17B, in order to acquire signals from a super pixel at the location of (m1+1, 2), the second switching device 123-2 connected to the second data line DL(2) and the third switching device 123-3 connected to the third data line DL(3) may be switched on at the same time, while turn-on signals are applied to the gate line GL(m1+1) of the (m1+1)-th row and the gate line GL(m1+2) of the (m1+2)-th row at the same time, so that signals can be acquired at the same time from four pixels at the locations of (m1+1, 2), (m1+1, 3), (m1+2, 2), and (m1+2, 3). The signals acquired from the four pixels may be input to the readout circuit 124. Signals of the remaining pixels may also be acquired in the same manner as described above.

Meanwhile, in the case of a region of uninterest, general gate scanning may be performed, and in the general gate scanning, binning sets of super pixels are not formed. For example, by switching on the first switching device 123-1 connected to the first data line DL(1) and then switching on the second switching device 123-2 connected to the second data line DL(2) while sequentially applying a turn-on signal to the first gate line GL(1) and the second gate line GL(2), signals may be acquired from pixels at the locations of (1, 1), (1, 2), (1, 3), . . . , (1, n), and from pixels at the locations of (2, 1), (2, 2), (2, 3), . . . , (2, n), sequentially. The signals acquired from the pixels may be input to the readout circuit 124.

Meanwhile, the first switching device 123-1 to the n-th switching device 123-$n$ may be switched on at the same time or at regular time intervals. Also, after the signals of the (m1+1)-th and (m1+2)-th rows are acquired, signals of the remaining rows may be acquired by grouping two adjacent rows sequentially.

Meanwhile, the binning pattern may be changed to a binning pattern as shown in FIG. 17B, and the X-ray detector 120 may acquire signals through the same method according to the binning pattern.

Also, in the current example, likewise, the readout circuit 124 may include the amplifiers 124*a* and the multiplexers 124*c*. In this case, the multiplexer 124*c* may be n-to-1 MUX. However, the multiplexer 124*c* may be n-to-p MUX, wherein p is the number of columns included in a binning set.

In the example of FIG. 18, the amplifiers 124*a* may be located at the input terminals of the multiplexer 124*c*, however, the amplifiers 124*a* may be located at the output terminals of the multiplexer 124*c* in order to improve noise characteristics.

Alternatively, it is also possible to output signals acquired from the individual columns in parallel, without providing a multiplexer.

Figure 20:
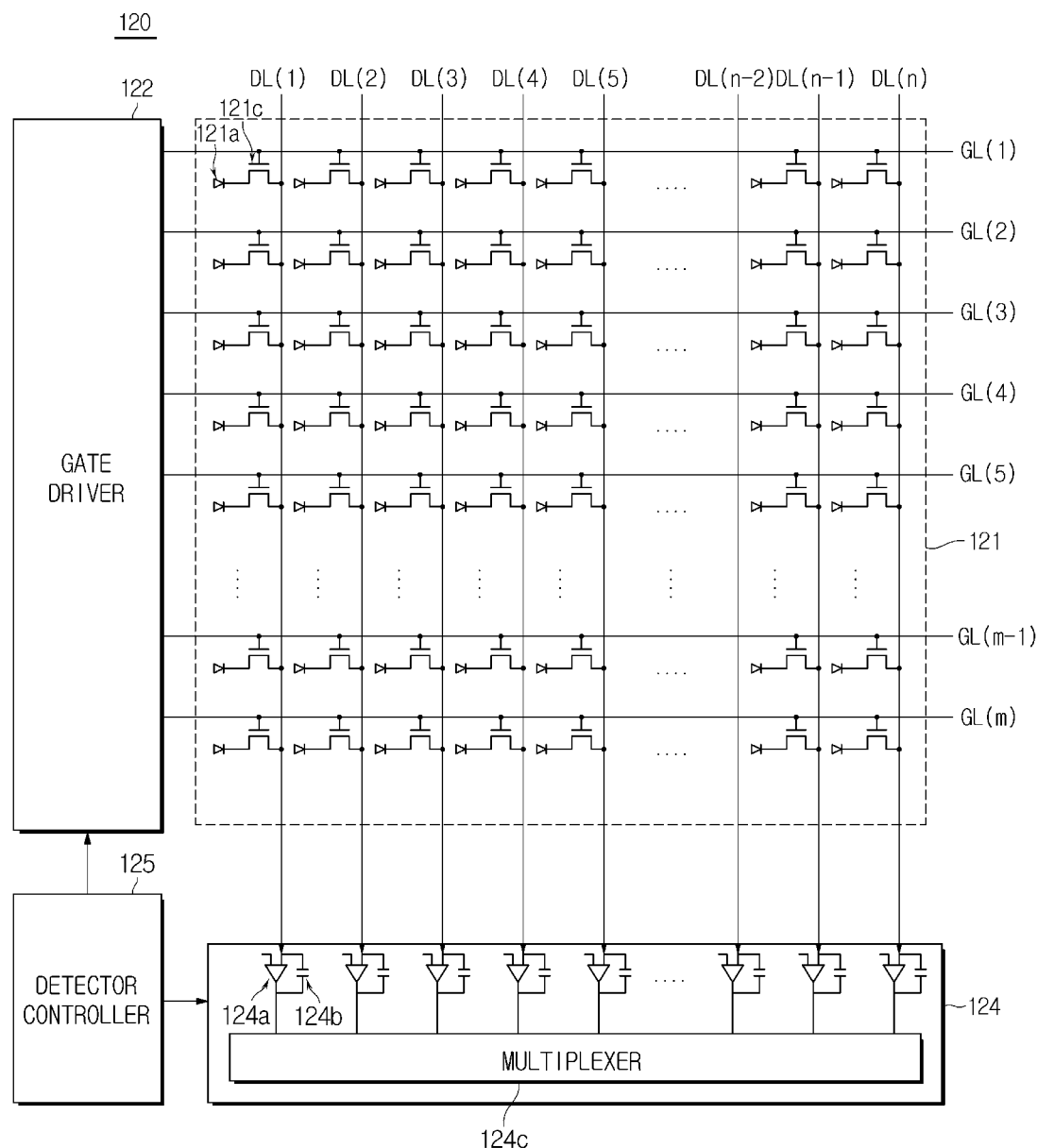
FIG. 20 shows a structure of an X-ray detector according to another example.

FIG. 20 shows a structure of the X-ray detector 120 according to another example.

In the example of the X-ray detector 120 described above, the switching unit 123 is provided between the detection region 121 and the readout circuit 124, whereas the X-ray detector 120 according to another example synchronizes turn-on signals with respect to a region of interest by including a multiplexer 124c being n-to-p MUX (n is the number of columns included in a binning set) in the readout circuit 124, without providing the switching unit 123, as shown in FIG. 20. In the example of FIG. 20, p=2.

More specifically, if a signal acquired from the first data line DL(1) to a signal acquired from the n-th data line DL(n) are input to the multiplexer 124c, the multiplexer 124c may output the signal acquired from the first data line DL(1) and a signal acquired from the second data line DL(2) at the same time, and then, output a signal acquired from the third data line DL(3) and a signal acquired from the fourth data line DL(4) at the same time with a predetermined time interval. In the same manner, the multiplexer 124c may output a signal acquired from a (n−1)-th data line DL(n−1) and a signal acquired from the n-th data line DL(n).

The amplifiers 124a may be provided at the input terminals of the multiplexer 124c, as shown in FIG. 20. However, if the amplifiers 124a are provided at the output terminals of the multiplexer 124c so that signals acquired from two data lines are multiplied and then pass through the amplifiers 124a, noise characteristics of an X-ray image can be improved.

So far, the structure and operations of the X-ray detector 120 that performs binning scanning on a region of interest to acquire an X-ray image have been described. Hereinafter, a method of reconstructing a high-resolution X-ray image using an X-ray image of a region of interest subject to binning scanning will be described.

Figure 21:
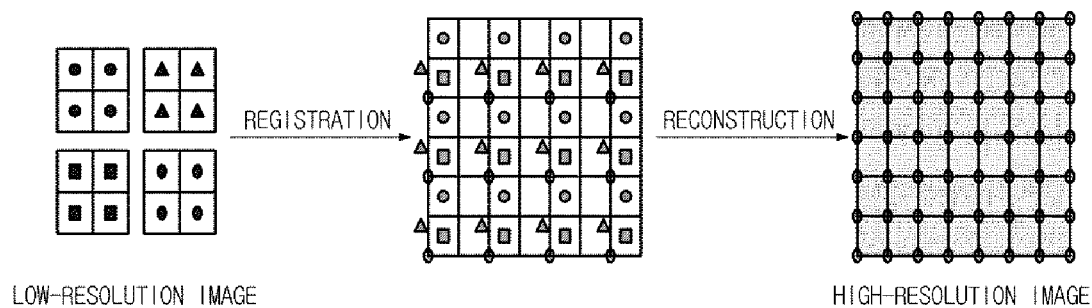
FIG. 21 is a view for describing a process in which an image processor reconstructs a binning-scanned image of a region of interest.

FIG. 21 is a view for describing a method in which the image processor 130 reconstructs a binning-scanned image of a region of interest.

The image processor 130 may reconstruct a high-resolution X-ray image using a plurality of low-resolution X-ray images acquired by the X-ray detector 120. In order to reconstruct a high-resolution X-ray image, the image processor 130 may use a super resolution image reconstruction method.

The super resolution image reconstruction method is also called a high resolution image reconstruction method. However, the image processor 130 may use any other method for reconstructing a high-resolution X-ray image using a plurality of low-resolution X-ray images.

The super resolution image reconstruction method is a method of creating a high-resolution image using several low-resolution images having different information about a scene. For example, if low-resolution images having various binning patterns shifted by 1 pixel or ½ pixel in the horizontal or vertical direction are acquired, the images are combined to create a high-resolution image.

The X-ray detector 120 may acquire a plurality of low-resolution X-ray images having a binning pattern that is different from that shown in FIG. 17A, and the image processor 150 may reconstruct a high-resolution X-ray image using the low-resolution X-ray images. For example, the X-ray detector 120 may acquire a plurality of low-resolution X-ray images having a binning pattern shifted by 1 pixel in the horizontal direction, as shown in FIG. 17B, or a binning pattern shifted in the vertical direction, and having different pixel information about the same scene, and the image processor 130 may reconstruct a high-resolution X-ray image using the plurality of low-resolution X-ray images.

As shown in FIG. 21, in order to create a high-resolution image, registration and reconstruction may be performed.

The registration is used to obtain geometrical alignment correlation between low-resolution images. For example, if the X-ray detector 120 has acquired four low-resolution X-ray images having different binning patterns shifted by 1 pixel in the horizontal and vertical directions, registration may be applied to obtain alignment correlation as shown in FIG. 21.

Thereafter, by applying a spatial domain method of analyzing correlation between a low-resolution image and a high-resolution image in a spatial domain to reconstruct a high-resolution image using a low-resolution image, or a frequency domain method of analyzing correlation between a low-resolution image and a high-resolution image in a frequency domain to reconstruct a high-resolution image using a low-resolution image, pixel information is changed to be suitable for a high-resolution (HR) grid. Then, restoration, such as De-noising or De-blurring, may be applied.

Accordingly, the high-resolution X-ray image of the region of interest can be displayed without having a level difference.

Hereinafter, a control method of an X-ray imaging apparatus according to an embodiment of the present disclosure will be described.

FIGS. 22A to 24 are flowcharts illustrating control methods of an X-ray imaging apparatus. The X-ray imaging apparatus 100 according to the embodiment as described above can perform the control methods of the X-ray imaging apparatus.

Figure 22A:
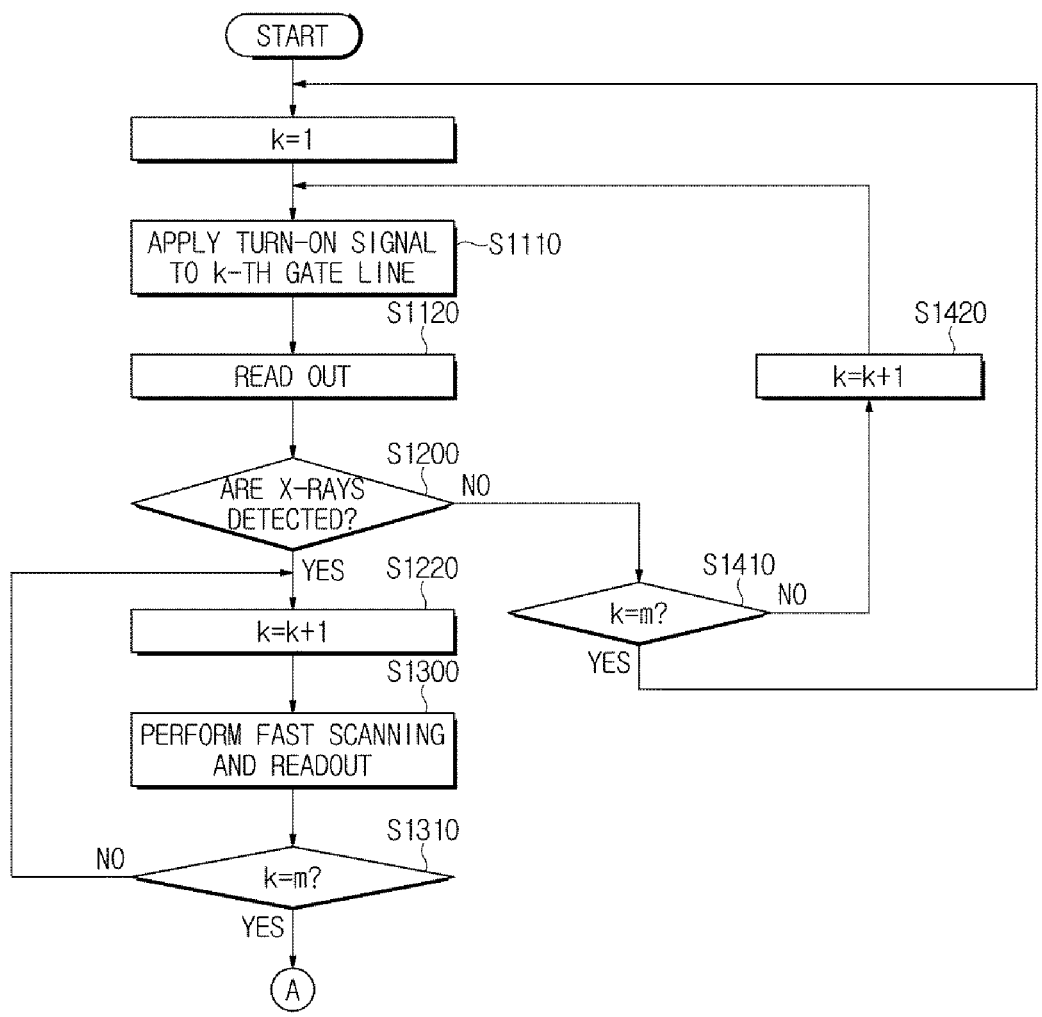
FIGS. 22A to 24 are flowcharts illustrating control methods of an X-ray imaging apparatus when operation of detecting X-rays is performed.

Referring to FIG. 22A, the X-ray imaging apparatus 100 may apply a turn-on signal for turning on the transistors 121c to the first gate line GL(1) to the m-th gate line GL(m) of the X-ray detection region, sequentially, in order to detect X-rays irradiated from the X-ray source 110, in operation S1110. Then, the X-ray imaging apparatus 100 may detect signals output from the n data lines DL of each gate line GL, in operation S1120. The X-ray imaging apparatus 100 may detect X-rays based on the output signals. A process of detecting X-rays from the data lines DL is called readout. A turn-on time period for which the transistors 121c of the individual gate lines GL are turned on may be longer than or equal to a threshold time period, wherein the threshold time period may be 3 μs. The threshold time period may have been set in advance by a user, or stored in advance in a storage unit (not shown).

Successively, if X-rays are detected from a certain gate line (for example, a gate line GL(m1)), in operation 1200, the X-ray imaging apparatus 100 may set the gate line GL(m1) to an X-ray detection line, and perform fast scanning on the lower gate line GL(m1+1) (a first reference line) of the X-ray detection line, in operation S1300. Fast scanning is turning on transistors of each gate line GL for a time period that is shorter than the threshold time period to read out signals from n pixels. Then, the X-ray imaging apparatus 100 may apply a turn-on signal to the next gate line GL, in operation S1220, until a voltage is applied to the final gate line GL(m), in operation S1310. However, if no X-rays are detected from the gate line GL(m1) in operation 1200, the X-ray imaging apparatus 100 may apply a turn-on signal to the transistors 121c of the next gate line GL(m1+1) in operations S1410, S1420, and S1110, detect signals output from the n data lines DL of each gate line GL, in operation S1120, and detect X-rays in operation S1200, to perform slow scanning. If a user has designated a region on which slow scanning will be performed and a region on which fast scanning will be performed, the X-ray imaging apparatus 100 may repeatedly perform slow scanning and fast scanning on the designated regions to detect X-rays.

Figure 22B:
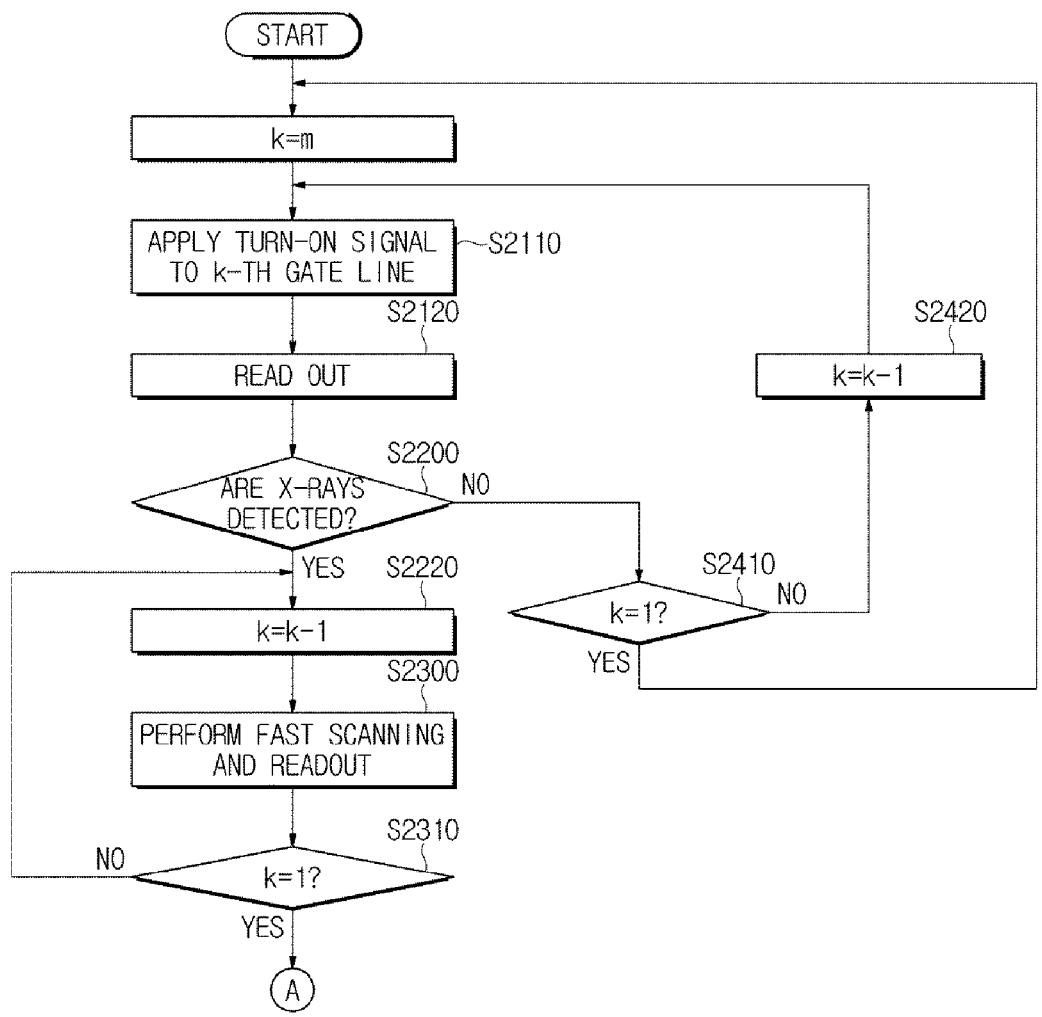

Meanwhile, a control method of the X-ray imaging apparatus 100 according to another embodiment of the present disclosure is shown in FIG. 22B. Referring to FIG. 22B, in order to detect X-rays irradiated from the X-ray source 110, the X-ray imaging apparatus 100 may apply a turn-on signal for turning on the transistors 121c to the m-th gate line GL(m) to the first gate line GL(1) of the X-ray detection region, in reverse order, in operation S2110, and detect signals output from the n data lines DL of each gate line GL, in operation S2120. In this case, a turn-on time period for which the transistors 121c of each gate line GL are turned on may be longer than or equal to a threshold time period, wherein the threshold time period may be 3 µs. The threshold time period may have been set in advance by a user, or stored in advance in a storage unit (not shown).

Successively, if X-rays are detected from a certain gate line (for example, a gate line GL(m2+1)) in operation S2200, the X-ray imaging apparatus may set the gate line GL(m2+1) to an X-ray detection line, and may perform fast scanning on the upper gate line GL(m2) (a second reference line) of the X-ray detection line, in operation S2300. In this case, a turn-on time period for which the transistors 121c of each gate line GL are turned on for fast scanning may be set to be longer than or equal to the threshold time period. Then, the X-ray imaging apparatus 100 may apply a turn-on signal to the upper gate line GL, in operation S2220, until a voltage is applied to the first gate line GL(1) in operation S2310. However, if no X-rays are detected from the (m2+1)-th gate line GL(m2+1) in operation S2200, the X-ray imaging apparatus 100 may apply a turn-on signal to the transistors 121c of the upper gate line GL(m2) in operations S2410, S2420, and S2110, detect signals output from the n data lines DL of each gate line GL, in operation S2120, and detect X-rays in operation S2200, to perform slow scanning. Meanwhile, the first reference line and the second reference line may be arbitrarily set, instead of the lower gate line GL(m1+1) of the m1-th gate line GL(m1) from which X-rays have been detected and the upper gate line GL(m2+1) of the m2-th gate line GL(m2) from which X-rays have been detected. That is, the first and second reference lines, which are reference rows or reference gate lines GL for dividing a region for fast scanning from a region for slow scanning, may have been set in advance by a user or a manufacturer. However, the first and second reference lines may be set to any gate line GL(m1+a1) among the lower gate lines of the gate line GL(m1) from which X-rays have been detected, and any gate line GL(m2+a2) among the upper gate lines of the gate line GL(m2) from which X-rays have been detected.

Figure 23A:
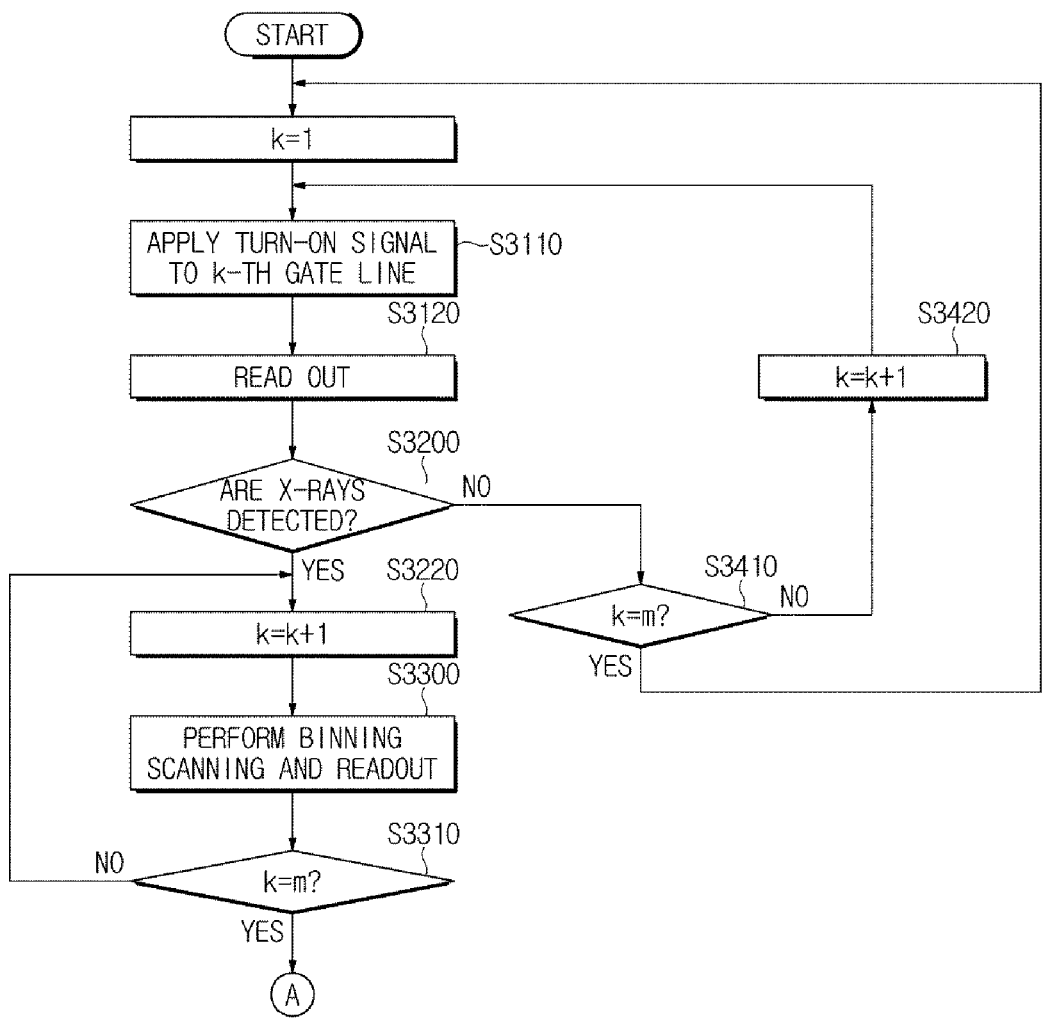

Meanwhile, a control method of the X-ray imaging apparatus 100 according to another embodiment of the present disclosure is shown in FIG. 23A. Referring to FIG. 23A, in order to detect X-rays irradiated from the X-ray source 110, the X-ray imaging apparatus 100 may apply a turn-on signal for turning on the transistors 121c to the first gate line GL(1) to the m-th gate line GL(m) of the X-ray detection region, sequentially, in operation S3110, and detect signals output from the n data lines DL of each gate line GL, in operation S3120. In this case, the turn-on signal for turning on the transistors 121c of each gate line GL may be applied successively. While the turn-on signal is applied, signals may be acquired from the first data line DL(1) to the n-th data line DL(n).

Successively, if X-rays are detected from a certain gate line (for example, a gate line GL(m1)), in operation S3200, the X-ray imaging apparatus 100 may set the gate line GL(m1) to an X-ray detection line, and perform binning scanning on the lower gate line GL(m1+1) (a first reference line) of the X-ray detection line, in operation S3300. The binning scanning is performing pixel binning of simultaneously applying signals to gate lines GL of pixels constituting a super pixel to acquire a low-resolution X-ray image. If no X-rays are detected from the gate line GL(m1) in operation S3200, the X-ray imaging apparatus 100 may apply a turn-on signal to the transistors 121c of the next gate line GL(m1+1) in operations S3410, S3420, and S3110, detect signals output from the n data lines DL of each gate line GL, in operation S3120, and detect X-rays in operation S3200, to perform general scanning.

Figure 23B:
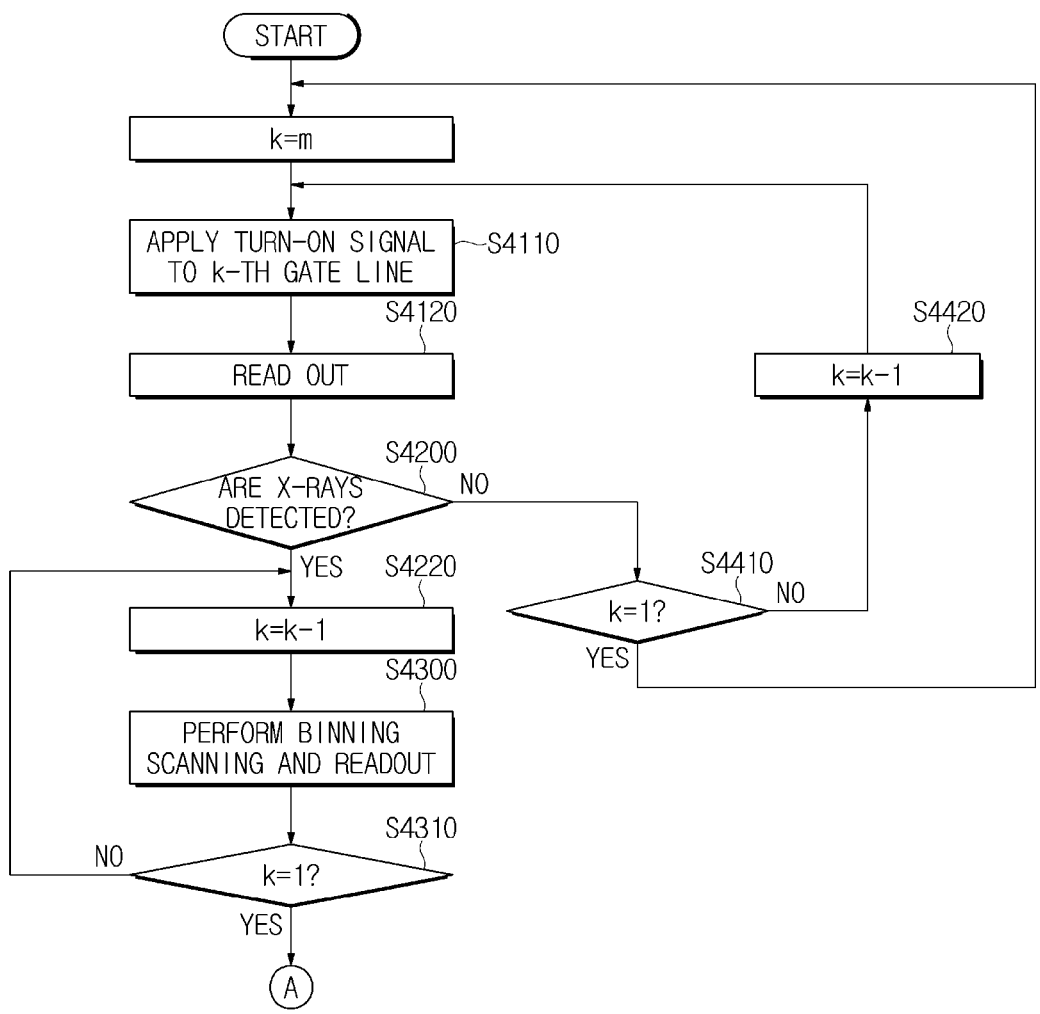

Meanwhile, a control method of the X-ray imaging apparatus 100 according to another embodiment of the present disclosure is shown in FIG. 23B. Referring to FIG. 23B, in order to detect X-rays irradiated from the X-ray source 110, the X-ray imaging apparatus 100 may apply a turn-on signal for turning on the transistors 121c to the m-th gate line GL(m) to the first gate line GL(1) of the X-ray detection region, in reverse order, in operation S4110, and detect signals output from the n data lines DL of each gate line GL, in operation S4120.

Successively, if X-rays are detected from a certain gate line (for example, a gate line GL(m2+1)), in operation S4200, the X-ray imaging apparatus 100 may set the gate line GL(m2+1) to an X-ray detection line, and perform binning scanning on the upper gate line GL(m2) (a second reference line) of the X-ray detection line, in operation S4300. In this case, turn-on times may be synchronized between the gate lines GL on which binning scanning is performed. Synchronizing turn-on times means applying turn-on signals at the same time. If a group of pixels of which turn-on times are synchronized is referred to as a binning set, a size of a binning set may have been set in advance by a user, or stored in advance in a storage unit (not shown).

Also, the X-ray imaging apparatus 100 may apply a turn-on signal to the upper gate line GL, in operation S4220, until a voltage is applied to the first gate line GL(1), in operation S4310. However, if no X-rays are detected from the (m2+1)-th gate line GL(m2+1) in operation S4200, the X-ray imaging apparatus 100 may apply a turn-on signal to the transistors 121c of the upper gate line GL(m2) in operations S4410, S4420, and S4110, detect signals output from the n data lines DL of each gate line GL in operation S4120, and detect X-rays in operation S4200, to perform general gate scanning.

For example, if 2×2 binning scanning is performed on the (m1+1)-th gate line GL(m1+1), (m1+1, 1), (m1+1, 2), (m1+2, 1), and (m1+2, 2) may be set to a super pixel, and turn-on signals for turning on the transistors 112c of the (m1+1)-th and (m1+2)-th rows may be applied to the (m1+1)-th and (m1+2)-th rows at the same time. In order to acquire signals from a super pixel at the location of (m1+1, 1), the X-ray imaging apparatus 100 may turn on the first switching device 123-1 connected to the first data line DL(1) and the second switching device 123-2 connected to the second data line DL(2) at the same time, while turn-on signals are applied to the gate line GL(m1+1) of the (m1+1)-th row and the gate line GL(m1+2) of the (m1+2)-th row at the same time, thereby acquiring signals from four pixels at the locations of (m1+1, 1), (m1+1, 2), (m1+2, 1), and (m1+2, 2) at the same time. The signals acquired from the four pixels may be input to the readout circuit 124.

As another example, if (m2−m1)×2 binning scanning is performed on the (m1+1)-th gate line GL(m1+1), (m1+1, 1), (m1+1, 2), (m1+2, 1), (m1+2, 2), (m1+3, 1), (m1+3, 2), . . . , (m2−1, 1), (m2−2, 2), (m2, 1), and (m2, 2) may be set to a super pixel, and turn-on signals for turning on the transistors 112c of the (m1+1)-th gate line GL(m1+1) to the m2-th gate line GL(m2) may be applied to the (m1+1)-th gate line GL(m1+1) to the m2-th gate line GL(m2) at the same time. A method of acquiring signals from a plurality of pixels at the same time is the same method as that used when 2×2 binning scanning is performed on the (m1+1)-th gate line GL(m1+1).

Also, a method of acquiring signals from a super pixel at another location is also the same method as described above, and accordingly, a detailed description thereof will be omitted.

Meanwhile, the 2×2 binning scanning and the (m2−m1)×2 binning scanning are examples of binning scanning that is performed by the X-ray imaging apparatus 100, and a size of a binning set can be adjusted in consideration of the properties of an object, a purpose of radiography, etc.

Figure 24:
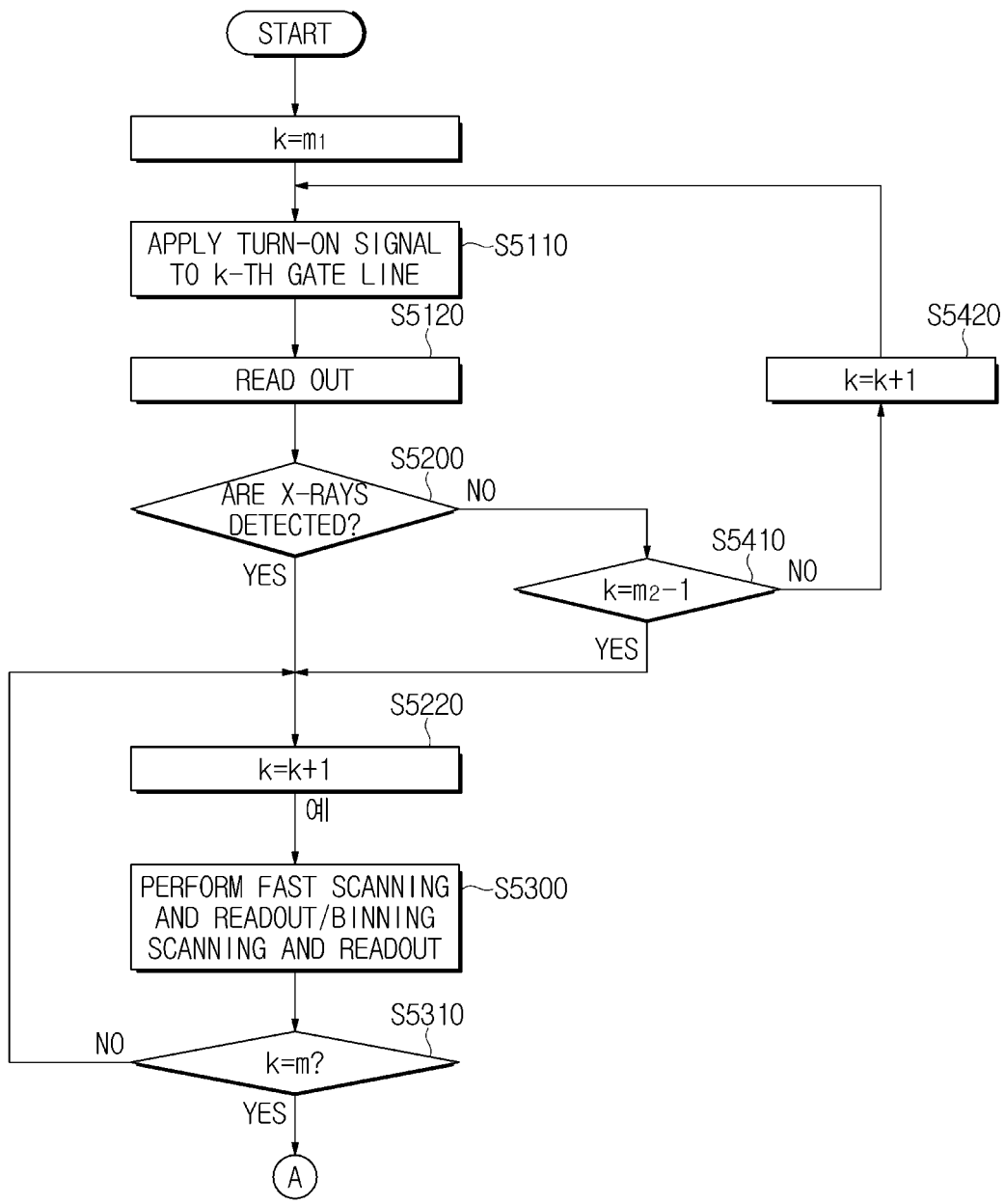

Meanwhile, a control method of the X-ray imaging apparatus 100 according to another embodiment of the present disclosure is shown in FIG. 24. Referring to FIG. 24, in order to detect X-rays, the X-ray imaging apparatus 100 may perform slow scanning or general scanning on the m1-th gate line GL(m1) to the (m2−1)-th gate line GL(m2−1) that are predetermined gate lines, sequentially, in operations S5110 and S5120, and perform fast scanning or binning scanning from the m2-th gate line GL(m2) that is a predetermined gate line, in operation S5300. In this case, the (m2−1)-th gate line GL(m2−1) is a threshold gate line on which slow scanning or general scanning is performed. The m2-th gate line GL(m2) to the m-th gate line GL(m) may have been set in advance such that fast scanning/binning scanning and readout are performed on the m2-th gate line GL(m2) to the m-th gate line GL(m) in operations S5410 and S5420. However, if X-rays are detected from a gate line (for example, a gate line GL(md)) among the m1-th gate line GL(m1) to the (m2−1)-th gate line GL(m2−1), in operation S5200, the setting may be changed such that fast scanning or binning scanning is performed on the gate line GL(md+1) after the gate line GL(md) from which X-rays have been detected, in operation S5220. That is, when the (m2−1)-th gate line ends to being scanned or when X-rays are detected, fast scanning or binning scanning may be performed, and readout for detecting X-rays may be performed during scanning, in operations S5300 and S5310.

Meanwhile, FIG. 24 relates to the case of applying turn-on signals to detect X-rays sequentially, however, the same method as described above may be applied to the case of applying a turn-on signal from the m-th gate line GL(m) to the first gate line GL(1) in reverse order. In this case, slow scanning or general scanning may have been set in advance to be performed on the m4-th to m3-th gate lines, and fast scanning or binning scanning may have been set in advance to be performed on the (m3−1)-th to m1-th gate lines.

That is, fast scanning or binning scanning may be performed based on the m1 to m4-th gate lines GL that have been arbitrarily set. In this case, a gate line GL among the m1 and m2 gate lines GL, and the m3 and m4 gate lines GL may be set to be X-ray detection lines.

Figure 25:
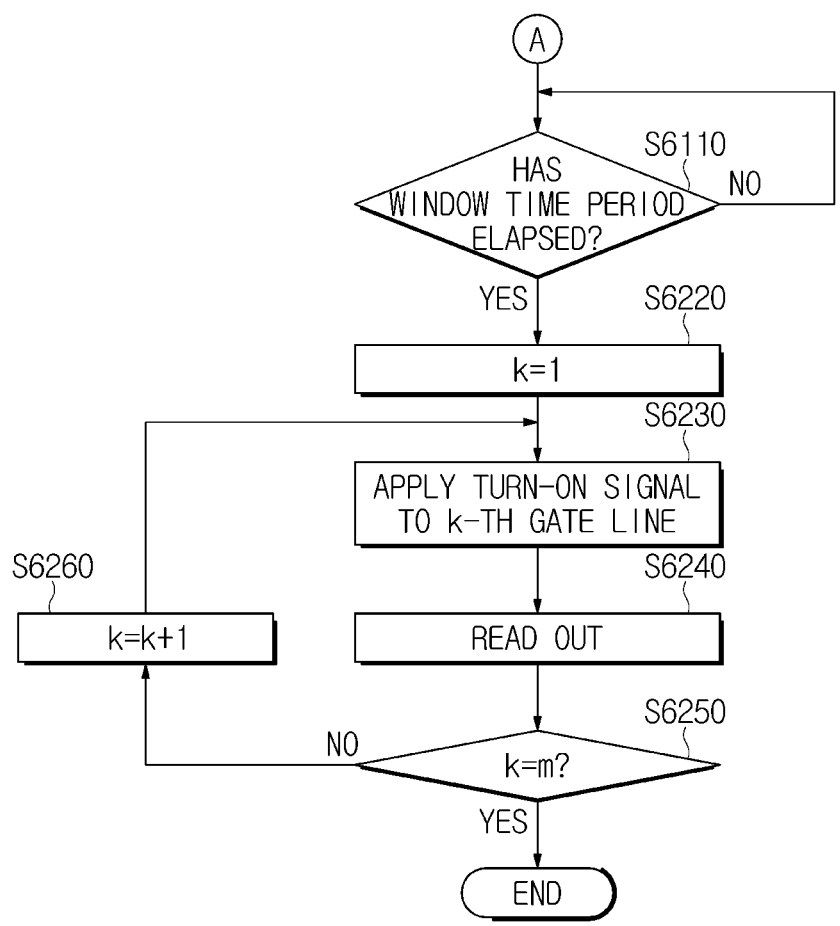
FIG. 25 is a flowchart illustrating operation of reading out actual X-ray image signals after operation of detecting X-rays is performed.

Meanwhile, after operation of detecting X-rays is performed, operation of reading out signals of an actual X-ray image may be further performed. FIG. 25 is a flowchart illustrating operation of reading out actual X-ray image signals after operation of detecting X-rays is performed.

If a window time period set by a user has elapsed after operation of detecting X-rays is completed (A), in operation S6110, the X-ray detector 120 may again apply a turn-on signal sequentially from the first gate line GL(1), in operations S6220 and S6230, and read out signals of an actual X-ray image, in operation S6240. In this case, a turn-on time period of the turn-on signal is set to a time period enough to read out actual X-ray image signals, and may be longer than or equal to a threshold time period, wherein the threshold time period may be 3 μs. Then, the X-ray detector 120 may apply a turn-on signal up to the final gate line GL(m) sequentially, in operations S6250, S6260 and S6230, and read out actual X-ray image signals, in operation S6240. Likewise, the X-ray detector 120 may apply a turn-on signal in reverse order from the final gate line GL(m), and read out actual X-ray image signals.

According to the X-ray imaging apparatus 100 and the control method thereof, by performing slow scanning on a predetermined region and performing fast scanning on the remaining region, it is possible to reduce signal loss and a level difference of an X-ray image during reading-out of actual X-ray image signals, without having to perform image post processing for reducing an image level difference.

According to the X-ray imaging apparatus 100 and the control method thereof, by providing a separate region for slow scanning or general scanning to determine existence of X-rays, and performing fast scanning or binning scanning on the remaining region, it is possible to reduce signal loss and a level difference of an X-ray image during reading-out of actual X-ray image signals, without having to perform image post processing for reducing an image level difference.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. An X-ray detector, comprising:
   a scintillator configured to convert X-rays into visible rays;
   an X-ray detection region including a plurality of photodiodes connected to each other by a plurality of gate lines for each row, and by a plurality of data lines for each column and configured to convert the visible rays into electrical signals;
   a gate driver configured to apply a turn-on signal to the gate lines sequentially;
   a readout circuit configured to read out the electrical signals converted by the photodiodes and transmitted through the data lines; and
   a detector controller controlling if the readout circuit detects an existence of an electrical signal from the photodiode connected to one gate line of one region when the gate driver applies the turn-on signal to the one gate line, the gate driver to apply another turn-on signal having a turn-on time period that is different from a turn-on time period of the one region, to the gate lines of another region, and
   the one region and the other regions are divided based on the one gate line.

2. The X-ray detector according to claim 1, wherein if the readout circle detects an existence of an electrical signal from the photodiode connected to the one gate line when the gate driver applies the turn-on signal to the one gate line, the detector controller controls the gate driver to apply a turn-on signal having a turn-on time period that is shorter than a turn-on time period of the one region, to the gate lines of the other region.

3. The X-ray detector according to claim 2, wherein if a predetermined time period elapses, the detector controller controls the gate driver to again applies the turn-on signal to the gate lines of the one region.

4. The X-ray detector according to claim 1, wherein if the readout circuit detects an existence of an electrical signal from the photodiode connected to one gate line in one region when the gate driver applies the turn-on signal to the one gate line, the detector controller controls the gate driver to use a changed turn-on time period of the turn-on signal that is applied to another gate line adjacent to the one gate line.

5. An X-ray detector, comprising:
a scintillator configured to convert X-rays into visible rays;
an X-ray detection region including a plurality of photodiodes connected to each other by a plurality of gate lines for each row, and by a plurality of data lines for each column and configured to convert the visible rays into electrical signals;
a gate driver configured to apply a turn-on signal to the gate lines sequentially;
a readout circuit configured to read out the electrical signals converted by the photodiodes and transmitted through the data lines; and
a detector controller configured to control the gate driver to apply a turn-on signal having a first turn-on time period to the gate lines of a first region of the X-ray detection region, and applies the turn-on signal having a second turn-on time period that is shorter than the first turn-on time period to the gate lines of a second region of the X-ray detection region.

6. The X-ray detector according to claim 5, wherein the readout circuit is configured to detect an existence of an electrical signal from the photodiode connected to one gate line in the first region when the gate driver applies the turn-on signal to the one gate line.

7. The X-ray detector according to claim 5, wherein the first region is located at least one of above and below the second region.

8. An X-ray detector, comprising:
a scintillator configured to convert X-rays into visible rays;
an X-ray detection region including a plurality of photodiodes connected to each other by a plurality of gate lines for each row, and by a plurality of data lines for each column and configured to convert the visible rays into electrical signals;
a gate driver configured to apply a turn-on signal to the gate lines sequentially;
a readout circuit configured to read out the electrical signals converted by the photodiodes and transmitted through the data lines; and
a detector controller controlling if the readout circuit detects an existence of an electrical signal from the photodiode connected to one gate line, the gate driver to reduce a turn-on time period of the turn-on signal, and again apply the turn-on signal to the plurality of gate lines if a predetermined time period elapses,
Wherein the turn-on time period of the turn-on signal that is again applied is longer than the turn-on time period of the turn-on signal that has been reduced.

9. An X-ray detector, comprising:
a scintillator configured to convert X-rays into visible rays;
an X-ray detection region including a plurality of photodiodes connected to each other by a plurality of gate lines for each row, and by a plurality of data lines for each column and configured to convert the visible rays into electrical signals;
a gate driver configured to apply a turn-on signal to the gate lines sequentially;
a readout circuit configured to read out the electrical signals converted by the photodiodes and transmitted through the data lines, and
a detector controller controlling if the readout circuit detects an existence of an electrical signal from the photodiode connected to one gate line of one region when the gate driver applies one turn-on signal to the one gate line, the gate driver to apply another turn-on signal whose turn-on time is synchronized to a predetermined time to the gate lines of another region, and
the one region and the other region are divided based on the one gate line.

10. The X-ray detector according to claim 9, wherein the one region is located at least one of above and below the other region.

11. The X-ray detector according to claim 9, wherein the detector controller is configured to control the gate driver to apply the other turn-on signal whose turn-on time is synchronized according to a predetermined binning pattern to the gate lines of the other region.

12. The X-ray detector according to claim 9, wherein if a predetermined time period elapses, the detector controller controls the gate driver to again apply the turn-on signal to the gate lines of the one region.

13. A control method of an X-ray detector comprising a scintillator configured to convert X-rays into visible rays, and a plurality of photodiodes connected to each other by a plurality of gate lines for each row, and by a plurality of data lines for each column and configured to convert the visible rays into electrical signals, the control method; comprising:
applying by a gate driver a turn-on signal to the gate lines sequentially;
reading out by a readout circuit the electrical signals converted by the photodiodes and transmitted through the data lines; and
if the readout circuit detects an existence of an electrical signal from the photodiode connected to one gate line of one region when the gate driver applies one turn-on signal to the one gate line, controlling the gate driver to apply another turn-on signal having a turn-on time period that is different from a turn-on time period of the one region to the gate lines of another region,
wherein the one region and the other region are divided based on the one gate line.

14. The control method according to claim 13, wherein the controlling the gate driver comprises, if the readout circuit detects an existence of an electrical signal from the photodiode connected to one gate line of one region when the gate driver applies one turn-on signal to the one gate line, controlling the detector controller to apply a turn-on signal having a turn-on time period that is shorter than a turn-on time period of the one region to the gate lines of the other region.

15. A control method of an X-ray detector comprising a scintillator configured to convert X-rays into visible rays, and a plurality of photodiodes connected to each other by a plurality of gate lines for each row, and by a plurality of data lines for each column and configured to convert the visible rays into electrical signals, the control method comprising:

applying by a gate driver a turn-on signal having a first turn-on time period to the gate lines of a first region sequentially;

reading out by a readout circuit the electrical signals converted by the photodiodes and transmitted through the data lines; and if the readout circuit detects an existence of an electrical signal from the photodiode connected to one gate line of the first region, controlling the gate driver to apply another turn-on signal having a second turn-on time period that is shorter than the first turn-on time period, to the gate lines of the second region.

16. The control method according to claim 15, wherein the first region is located at least one of above and below the second region.

17. A control method of an X-ray detector comprising a scintillator configured to convert X-rays into visible rays, and a plurality of photodiodes connected to each other by a plurality of gate lines for each row, and by a plurality of data lines for each column and configured to convert the visible rays into electrical signals, the control method comprising:

applying by a gate driver a turn-on signal to the gate lines sequentially;

reading out by a readout circuit the electrical signals converted by the photodiodes and transmitted through the data lines; and if the readout circuit detects an existence of an electrical signal from the photodiode connected to one gate line of one region when the gate driver applies one turn-on signal to the one gate line, controlling the gate driver to apply another turn-on signal whose turn-on time is synchronized to a predetermined time to the gate lines of another region, wherein the one region and the other region are divided based on the one gate line.

18. The control method according to claim 17, wherein the one region is located at least one of above and below the other region.

19. The control method according to claim 17, wherein the controlling the gate driver comprises controlling the gate driver to apply, if the readout circuit detects an existence of an electrical signal from the photodiode connected to one gate line of one region when the gate driver applies one turn-on signal to the one gate line, the other turn-on signal, which is synchronized to a predetermined binning pattern, to the gate lines of the other region.

* * * * *